(12) United States Patent
Buynak et al.

(10) Patent No.: US 6,303,592 B1
(45) Date of Patent: *Oct. 16, 2001

(54) 7-ALKYLIDENE CEPHALOSPORANIC ACID DERIVATIVES AND METHODS OF USING THE SAME

(75) Inventors: John D. Buynak; Brian Bachmann, both of Dallas, TX (US)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/818,967

(22) Filed: Mar. 14, 1997

Related U.S. Application Data

(62) Division of application No. 08/354,850, filed on Dec. 9, 1994, now Pat. No. 5,629,306.

(51) Int. Cl.⁷ ............ C07D 501/22; C07D 501/58; A61K 31/545
(52) U.S. Cl. ............ 514/206; 514/201; 514/204; 514/205; 514/207; 514/208; 514/209; 540/221; 540/222; 540/226; 540/227; 540/228; 540/229; 540/230
(58) Field of Search ............ 514/201, 204, 514/205, 206, 207, 208, 209; 540/221, 222, 226, 227, 228, 229, 230

(56) References Cited

U.S. PATENT DOCUMENTS

| | | | |
|---|---|---|---|
| 4,150,156 | 4/1979 | Beattie et al. | 424/246 |
| 4,459,405 * | 7/1984 | Hall | 544/28 |
| 4,547,371 | 10/1985 | Doherty et al. | 514/200 |
| 4,637,999 | 1/1987 | Doherty et al. | 514/201 |
| 4,992,541 | 2/1991 | Blacklock et al. | 540/221 |
| 5,077,286 | 12/1991 | Bissolino et al. | 514/201 |
| 5,126,446 | 6/1992 | Brown, Jr. et al. | 540/230 |
| 5,258,377 | 11/1993 | Marti et al. | 540/221 |
| 5,264,429 | 11/1993 | Maiti et al. | 514/202 |
| 5,348,952 | 9/1994 | Bissolino et al. | 514/202 |
| 5,356,888 | 10/1994 | Alpegiani et al. | 514/204 |
| 5,364,848 | 11/1994 | Doherty et al. | 514/201 |
| 5,446,037 | 8/1995 | Maiti et al. | 514/201 |

FOREIGN PATENT DOCUMENTS

| | | |
|---|---|---|
| 0041768 | 12/1981 | (EP) . |
| 0120613 | 10/1984 | (EP) . |
| 0210065 | 1/1987 | (EP) . |
| 0337704 | 10/1989 | (EP) . |
| WO91/09036 | 6/1991 | (WO) . |
| WO96/17848 | 6/1996 | (WO) . |
| WO96/17849 | 6/1996 | (WO) . |

OTHER PUBLICATIONS

Applegate, H.E., et al., "7–[2–Hydroxyethyl] Cephalosporanic Acid Derivatives", *Tetrahedron Letters*, No. 19, pp. 1637–1640, (1979).

Buynak, J.D., et al., "Synthesis and biological activity of 7–alkylidenecephems", *J. Med. Chem.*, 38, 1022–1034, (1995).

Buynak, J.D., et al., "Synthesis and mechanistic evaluation of 7–vinylidenecephem sulfones as B–lactamase inhibitors", *J. of Am. Chem. Soc.*, 116, 10955–10965, (1994).

Chandrasekaran, S., et al., "Synthesis of Substituted B–Lactams by Addition of Nitromethane to 6–Oxepenicillanates and 7–Oxocephalosporanates", *J. Org. Chem.*, vol. 42, No. 24, pp. 3972–3974, (1977).

Doherty, J.B., et al., "Inhibition of human leukeocyte elastase. 1. Inhibition by C–7–substituted cephalosporin tert–Butyl esters", *J. Med. Chem.*, 33, 2513–2521, (1990).

Finke, P.E., et al., "Inhibition of human leukocyte Elastase. 4. Selection of a substituted cephalosporin (L–658,758) as a topical aerosol", *J. Med. Chem.*, 35, 3731–3744, (1992).

Knight, W.B., et al., "Specificity, stability, and potency of monocyclic B–Lactam inhibitors of human leucocyte elastase", *Biochemistry*, 31, 8160–8170, (1992).

Navia, M.A., et al., "Crystallographic study of a B–lactam inhibitor complex with elastase at 1.84 A resolution", *Nature*, 327, 79–82, (1987).

Shah, S.K., et al., "Inhibition of human leukocyte Elastase. 3. Synthesis and activity of 3'–substituted cephalosporins", *J. Med. Chem.*, 33, 2529–2535, (1990).

Uyeo, S., et al., "Snythesis of (6R, 7R)–Phenylacetylmethyl–3(1–Methyl–1H–Tetrazol–5–yl) Thiomethyl–1–)xa–1–Dethiace phalosporanic Acid", *Heterocycles*, vol. 13, pp. 255–257, (1979).

Buynak, J.D., et al., "7–Alkylidenecephalosporin esters as Inhibitors of Human Leukocyte Elastase", *J. MEd. Chem.*, vol. 40, pp. 3423–3433, (1997).

* cited by examiner

*Primary Examiner*—Michael Pak
(74) *Attorney, Agent, or Firm*—Shwegman, Lundberg, Woessner & Kluth, P.A.

(57) ABSTRACT

Derivatives of 7-alkylidene cephalosporanic acid sulfone and the pharmaceutically active salts thereof are found to be potent inhibitors of β-lactamase enzymes.

13 Claims, No Drawings

7-ALKYLIDENE CEPHALOSPORANIC ACID DERIVATIVES AND METHODS OF USING THE SAME

This application is a divisional of U.S. patent application Ser. No. 08/354,850, filed Dec. 9, 1994 now U.S. Pat. No. 5,629,306.

This invention was made with Government support under Contract No. 5R01-GM-37774, awarded by the National Institutes of Health. The Government has certain rights to the invention.

BACKGROUND OF THE INVENTION

1. Field of the Invention

The present invention relates to novel compounds which are β-lactamase inhibitors, pharmaceutical compositions containing the same and methods of inhibiting β-lactamases. More specifically this invention is concerned with novel 7-alkylidene cephalosporins and pharmaceutically acceptable salts thereof.

2. Description of the Background

The most important mechanism of microbial resistance to β-lactam antibiotics is the bacterial production of β-lactamases, enzymes which hydrolytically destroy β-lactam antibiotics, such as penicillins and cephalosporins. This type of resistance can be transferred horizontally by plasmids that are capable of rapidly spreading the resistance, not only to other members of the same strain, but even to other species. Due to such rapid gene transfer, a patient can become infected with different organisms, each possessing the same β-lactamase.

β-lactamase enzymes have been organized into four molecular classes: A, B, C, and D based on amino acid sequence. Class A, which includes RTEM and the β-lactamase of *Staphylococcus aureus*, class C, which includes the lactamase derived from P99 *Enterobacter cloacae*, and class D are serine hydrolases. Class A enzymes have a molecular weight of about 29 kDa and preferentially hydrolyze penicillins. The class B lactamases are metalloenzymes and have a broader substrate profile than the proteins in the other classes. Class C enzymes include the chromosomal cephalosporinases of gram-negative bacteria and have molecular weights of approximately 39 kDa. The recently recognized class D enzymes exhibit a unique substrate profile which differs significantly from both class A and class C.

The class C cephalosporinases, in particular, are responsible for the resistance of gram-negative bacteria to a variety of both traditional and newly designed antibiotics. The Enterobacter species, which possess a class C enzyme, are now the third greatest cause of hospital-acquired infections in the United States. This class of enzymes often has poor affinities for inhibitors of the class A enzymes, such as clavulanic acid, a commonly prescribed inhibitor, and to common in vitro inactivators, such as 6-β-iodopenicillanate.

One strategy for overcoming rapidly evolving bacterial resistance is the synthesis and administration of β-lactamase inhibitors. Frequently, β-lactamase inhibitors do not possess antibiotic activity themselves and are thus administered together with an antibiotic. One example of such a synergistic mixture is "augmentin which is a registered trademark of the Smithkline Beechom Corporation", which contains the antibiotic amoxicillin and the β-lactamase inhibitor, clavulanic acid.

It is thus desirable to find novel β-lactamase inhibitors which can be coadministered with a β-lactam antibiotic.

SUMMARY OF THE INVENTION

Accordingly, one object of the present invention is to provide novel β-lactamase inhibitors.

It is another object of the present invention to provide pharmaceutical compositions useful for inhibiting a β-lactamase.

It is another object of the present invention to provide pharmaceutical compositions with increased β-lactam antibiotic activity.

It is another object of the present invention to provide methods of inhibiting a β-lactamase.

It is another object of the present invention to provide methods of enhancing the biological activity of a β-lactam antibiotic.

These and other objects, which will become apparent during the following detailed description, have been achieved by the inventors' discovery that compounds of the formula (1)

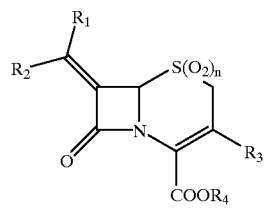

1 wherein n is 0 or 1 (the sulfide or the sulfone, respectively);

$R_1$ and $R_2$ are the same or different and are selected from the group consisting of
- a) hydrogen;
- b) linear or branched $C_{1-10}$-alkyl;
- c) halogen;
- d) hydroxy-$C_{1-10}$-alkyl;
- e) $C_{1-10}$-alkoxy;
- f) $C_{2-10}$-alkanoyloxy;
- g) $C_{2-10}$-alkene;
- h) $C_{2-10}$-alkene substituted with one or more groups selected from the group consisting of chlorine, fluorine, bromine or phenyl;
- i) $C_{1-10}$-alkoxycarbonyl;
- j) $C_{1-10}$-alkoxycarbamido;
- k) N-$C_{1-10}$-alkoxy-N-$C_{1-10}$-alkylaminocarbonyl;
- l) halo-$C_{1-10}$-alkyl;
- m) $C_{6-10}$-aryl;
- n) $C_{6-10}$-aryl substituted with one or more groups selected from the group consisting of ethyl, n-propyl, isopropyl, amino, methylamino and dimethylamino;
- o) a $C_{2-10}$-heterocycle having from 1–3 heteroatoms selected from the group consisting of O, N and S; and,
- p) —COOH or —COOY, wherein Y is pharmaceutically acceptable cation;

$R_3$ is selected from the group consisting of
1) —COOH;
2) chlorine or fluorine;
3) trifluoromethyl;
4) —CHO; and,
5) —$CH_2M$ where M is selected from the group consisting of
 - a) hydrogen;
 - b) halogen;

c) hydroxy;
d) $C_{1-10}$-alkoxy;
e) $C_{6-10}$-aryloxy;
f) $C_{6-10}$-aryl-$C_{1-10}$-alkoxy;
g) mercapto;
h) mercapto substituted with one or more groups selected from the group consisting of methyl, ethyl or phenyl;
i) $C_{2-10}$-acylthio;
j) $C_{2-10}$-acyloxy or carbamoyloxy;
k) $C_{2-10}$-acyloxy or carbamoyloxy substituted with one or more groups selected from the group consisting of —COOH, aminophenyl, phenyl, $C_{1-6}$-alkyl, chlorine, bromine or fluorine;
l) a quaternary ammonium salt;
m) amino or amido; and,
n) amino or amido substituted with one or more groups selected from the group consisting of $C_{1-10}$-alkyl groups;

$R_4$ is selected from the group consisting of
a) hydrogen; and,
b) pharmaceutically acceptable cations; are effective β-lactamase inhibitors.

DETAILED DESCRIPTION OF THE INVENTION

Thus, in a first embodiment, the present invention provides novel compounds of the formula (1)

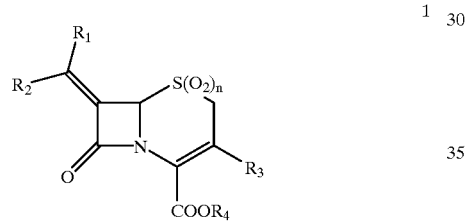

wherein n is 0 or 1;
$R_1$ and $R_2$ are the same or different and are selected from the group consisting of
a) hydrogen;
b) linear or branched $C_{1-10}$-alkyl, preferably, $C_{1-6}$-alkyl, more preferably, methyl, ethyl, n-propyl, isopropyl, n-butyl, t-butyl, n-pentyl, cyclopropyl, cyclopentyl, or cyclohexyl, most preferably t-butyl;
c) halogen, preferably Br or Cl;
d) hydroxy-$C_{1-10}$-alkyl, preferably, hydroxy-$C_{1-6}$-alkyl, more preferably, hydroxymethyl, 1-hydroxyethyl or 2-hydroxyethyl;
e) $C_{1-10}$-alkoxy, preferably, $C_{1-6}$-alkoxy, more preferably, t-butoxy or methoxy;
f) $C_{2-10}$-alkanoyloxy, preferably, $C_{2-6}$-alkanoyloxy, more preferably, acetoxy or propanoyloxy;
g) $C_{2-10}$-alkene, preferably, $C_{2-6}$-alkene, more preferably, ethylene, 1-propylene or 2-propylene;
h) substituted $C_{2-10}$-alkene, preferably, $C_{2-6}$-alkene, more preferably ethylene, 1-propylene or 2-propylene, wherein said substituents are one more groups selected from the group consisting of chlorine, fluorine, bromine or phenyl;
i) $C_{1-10}$-alkoxycarbonyl, preferably, $C_{1-6}$-alkoxycarbonyl, more preferably, methoxycarbonyl or t-butoxycarbonyl;
j) $C_{1-10}$-alkoxycacbamido, preferably, $C_{1-6}$-alkoxycarbamido, more preferably, methoxycarbamido, ethoxycarbamido or n-propoxycarbamido;
k) N-$C_{1-10}$-alkoxy-N-$C_{1-10}$-alkylaminocarbonyl, preferably, N-$C_{1-6}$-alkoxy-N-$C_{1-6}$-alkylaminocarbonyl, more preferably, N-methoxy-N-methylaminocarbonyl, N-ethoxy-N-methylaminocarbonyl, N-methoxy-N-ethylaminocarbonyl or N-ethoxy-N-ethylaminocarbonyl;
l) halo-$C_{1-10}$-alkyl, preferably, halo-$C_{1-6}$-alkyl, more preferably, chloromethyl, 1-chloroethyl or 2-chloroethyl;
m) $C_{6-10}$-aryl group, preferably, phenyl, tolyl, anisoyl, mesityl, and xylyl;
n) substituted $C_{1-10}$-alkyl, preferably, phenyl, tolyl, anisoyl, mesityl, and xylyl, wherein said substituents are one or more groups selected from the group consisting of ethyl, n-propyl, isopropyl, amino, methylamino and dimethylamino;
o) a $C_{2-10}$-heterocycle having from 1–3 heteratoms selected from the group consisting of O, N and S, preferably, triazolyl, triazinyl, oxazoyl, isoxazolyl, oxazolidinoyl, isoxazolidinoyl, thiazolyl, isothiazoyl, pyrazolyl, imidazolyl, pyrrolyl, pyrazinyl, pyridinyl, morpholinyl, quinolinyl, isoquinolinyl, indolyl, and pyrimidinyl, more preferably, pyridinyl; and,
p) —COOH or —COOY, wherein Y is a pharmaceutically acceptable cation, preferably, sodium, potassium, calcium, or any other pharmaceutically acceptable cation known in the art;

$R_3$ is selected from the group consisting of
1) —COOH;
2) Cl or F;
3) trifluoromethyl;
4) —CHO; and,
5) —$CH_2M$, wherein M is selected from the group consisting of
a) hydrogen;
b) halo, preferably F, Cl, Br, or I;
c) hydroxy;
d) $C_{1-10}$-alkoxy, preferably, $C_{1-6}$-alkoxy, more preferably, methoxy, ethoxy, n-propoxy or isopropoxy;
e) $C_{6-10}$-aryloxy, preferably, $C_{6-10}$-aryloxy, more preferably, phenoxy or naphthoxy;
f) $C_{6-10}$-aryl-$C_{1-10}$-alkoxy, preferably, $C_{6-10}$-aryl-$C_{1-6}$-alkoxy, more preferably, phenylmethoxy, 1-phenylethoxy or 2-phenylethoxy;
g) mercapto, preferably, thiol;
h) substituted mercapto, preferably, thiol, wherein said substituents are selected from the group consisting of methyl, ethyl or phenyl;
i) $C_{2-10}$-acylthio, preferably $C_{2-6}$-acylthio, more preferably, acetylthio or propanoylthio;
j) $C_{2-10}$-acyloxy or carbamoyloxy, preferably, $C_{2-6}$-alkanoyloxy, $C_{6-10}$-aryl-carbonyloxy, carbamoyloxy or thiocarbamoyloxy, more preferably, acetoxy or benzoyloxy;
k) substituted $C_{2-10}$-acyloxy or carbamoyloxy, preferably, $C_{2-6}$-alkanoyloxy, $C_{6-10}$-arylcarbonyloxy, N-$C_{1-6}$-alkylcarbamoyloxy, N,N-di-$C_{1-6}$-alkylcarbamoyloxy, thiocarbamoyloxy, N-$C_{1-6}$-alkylthiocarbamoyloxy or N,N-di-$C_{1-6}$-alkylthiocarbamoyloxy, more preferably, acetoxy, α-aminophenylacetoxy, benzoyloxy, benzyloxycarbonyloxy, succinoyloxy, N-methylcarbamoyloxy, N-ethylcarbamoyloxy, N,N-dimethylcarbamoyioxy, N,N-diethylcarbamoyloxy, N-methylthiocarbamoyloxy, N-ethylthiocarbamoyloxy, N,N-dimethylthiocarbamoyloxy, N,N-diethylthiocarbamoyloxy, wherein said substituents are one or more groups selected from the group consisting of —COOH, aminophenyl, phenyl, methyl, ethyl, chlorine, bromine or fluorine;
1) a quaternary ammonium salt, preferably trimethyl ammonium chloride or triethyl ammonium chloride;
m) amino or amido group, preferably —$NH_2$ or —$CONH_2$; and,
n) substituted amino or amido group, preferably —$NH_2$ or —$CONH_2$, wherein said substituents are one or two $C_{1-10}$-alkyl groups, preferably $C_{1-6}$-alkyl groups, more preferably, methyl, ethyl, n-propyl, isopropyl or n-butyl;

$R_4$ is selected from the group consisting of
a) hydrogen; and,
b) pharmaceutically acceptable cations, preferably, sodium, potassium or calcium.

In a preferred embodiment, n is 0, $R_2$ is hydrogen and $R_1$ is selected from the group consisting of t-butyl, phenyl, pyridyl, COMe and N-methyl-N-methoxy-aminocarbonyl.

In a more preferred embodiment, n is 0, $R_2$ is hydrogen, and $R_1$ is selected from the group consisting of $CO_2$-t-Bu and CHO.

In another preferred embodiment, n is 1, $R_2$ is hydrogen, and $R_1$ is selected from the group consisting of $CO_2Me$, $CH_2OH$ and t-butyl.

In another more preferred embodiment, n is 1, $R_2$ is hydrogen and $R_1$ is selected from the group consisting of phenyl, pyridyl and $CO_2$-t-butyl.

In another preferred embodiment, n is 0 and $R_1$ and $R_2$ are the same and are selected from the group consisting of bromine and chlorine.

In another preferred embodiment, n is 1 and $R_1$ and $R_2$ are the same and are selected from the group consisting of bromine and chlorine.

In another preferred embodiment, n is 0, $R_1$ is hydrogen, and $R_2$ is bromine.

In another preferred embodiment, n is 1, $R_1$ is hydrogen, and $R_2$ is selected from the group consisting of phenyl and bromine.

In a most preferred embodiment, n is 1, $R_1$ is pyridyl, $R_2$ is hydrogen, $R_3$ is —$CH_2OAc$ and $R_4$ is sodium.

Compounds according to formula (1) were obtained as follows. 7-Aminocephalosporanic acid (commercially available from Aldrich), esterified with diphenyl diazomethane (2), was treated with excess triethylamine and trifluoromethanesulfonic anhydride and the resultant trifluorosulfonyl imine was hydrolyzed to produce benzhydryl 7-oxocephalosporanate 3. (See Hagiwara, D. F.; Sawada, K.; Ohnami, T.; Aratani, M.; Hashimoto, M. *J. Chem Soc. Chem. Commun.* 1982, 578.) Due to its instability, 3 was used directly in the next step without purification.

The 7-alkylidenecephalosporanates 4 were prepared by treating 7-oxocephalosporanate 3 with the corresponding Wittig reagent at –78° C. Compounds 4 a–k were prepared in the standard manner with the exceptions of 4b, 4j, 4l, and 4m. Compound 4b required the addition of the Zn/Cu couple to 3 in the presence of $CCl_4$ and $PPh_3$ to lead to its formation. Compound 4j was prepared by the reduction of 4i with $NaCNBH_3$. Compound 4a was reduced by the Zn/Cu couple to produce monobromomethylenecephem 4l, which was further treated with t-BuLi and CuCN to give compound 4m as shown below.

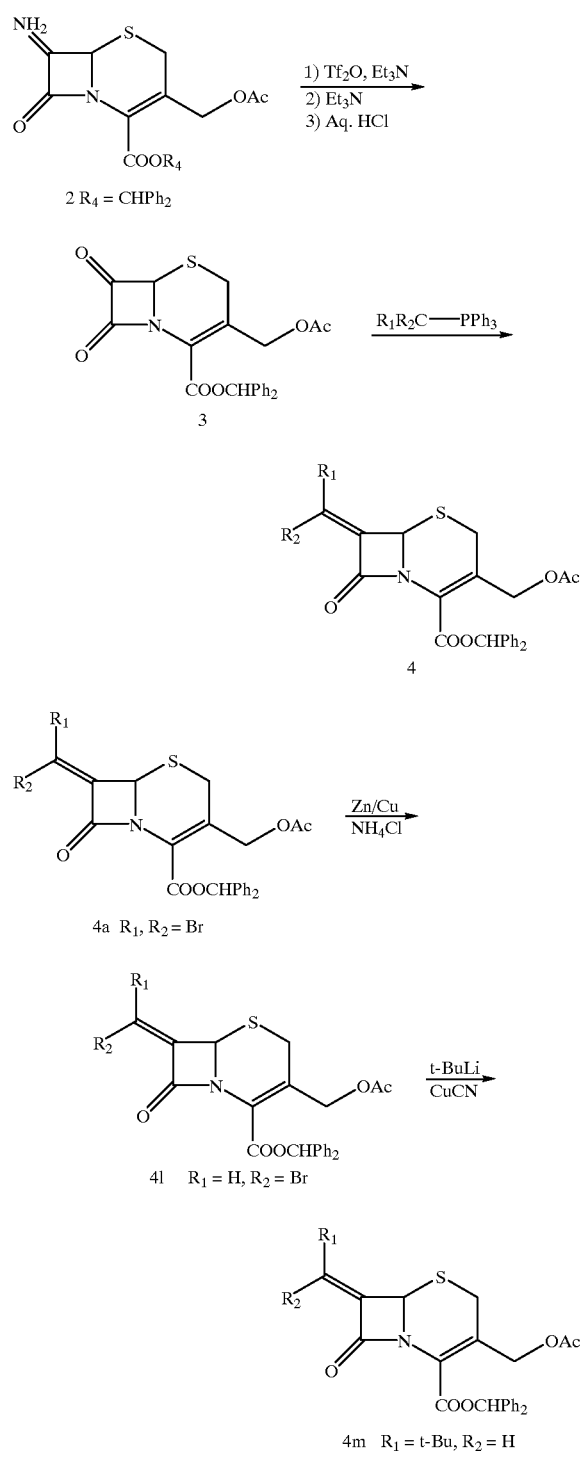

| no. | $R_1$ | $R_2$ |
|---|---|---|
| 4a | Br | Br |
| 4b | Cl | Cl |
| 4c | H | Ph |
| 4d | Ph | H |
| 4e | Py | H |

-continued

| | | |
|---|---|---|
| 4f | CO$_2$CH$_3$ | H |
| 4g | CO$_2$C(CH$_3$)$_3$ | H |
| 4h | COCH$_3$ | H |
| 4i | CHO | H |
| 4j | CH$_2$OH | H |
| 4k | CON(CH$_3$)(OCH$_3$) | H |
| 4l | H | Br |
| 4m | t-butyl | H |

Many of the compounds in the series 4 were oxidized with excess m-CPBA yielding the corresponding sulfones 5.

Deprotection of compounds 4 and 5 gave the corresponding sodium salts 6 and 7 as shown below.

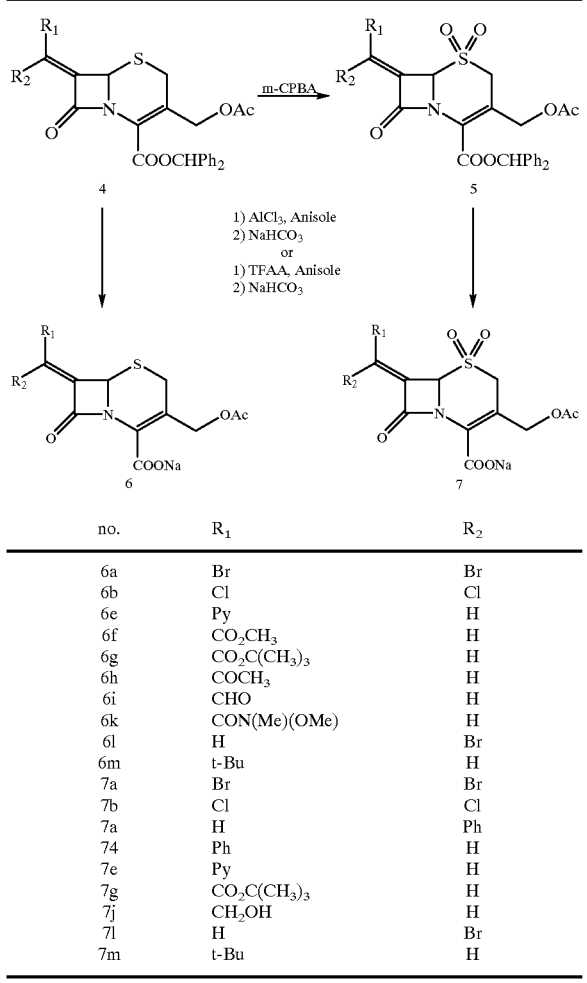

| no. | R$_1$ | R$_2$ |
|---|---|---|
| 6a | Br | Br |
| 6b | Cl | Cl |
| 6e | Py | H |
| 6f | CO$_2$CH$_3$ | H |
| 6g | CO$_2$C(CH$_3$)$_3$ | H |
| 6h | COCH$_3$ | H |
| 6i | CHO | H |
| 6k | CON(Me)(OMe) | H |
| 6l | H | Br |
| 6m | t-Bu | H |
| 7a | Br | Br |
| 7b | Cl | Cl |
| 7a | H | Ph |
| 74 | Ph | H |
| 7e | Py | H |
| 7g | CO$_2$C(CH$_3$)$_3$ | H |
| 7j | CH$_2$OH | H |
| 7l | H | Br |
| 7m | t-Bu | H |

Compounds containing R$_1$ and R$_2$ groups (i.e., alkoxy or alkene) not shown above may be synthesized by using an appropriate Wittig reagent R$_1$R$_2$C=PP$_3$. The Wittig reagents ROCH=PPh$_3$ and H$_2$C=CH—CH=PPh$_3$ may be used to make the 7-alkyoxymethylene and 7-alkenylmethylene compounds, respectively.

In addition to the Wittig reaction, the Peterson olefination procedure may be used to form 7-substituted methylene compounds from the oxocephalosporanate 3. For example, (RO)(SiMe$_3$)CHLi or (haloalkyl)(SiMe$_3$)CHLi may add to 3 to form the 7-alkoxymethylene or 7-halomethylmethylene compounds, respectively.

The 7-alkanoylmethylene species may be made by forming the vinyl anion and reacting it with a desirable alkanoyl halide. The vinyl anion may be made by a standard lithium-halogen (or magnesium-halogen) exchange reaction, for example, reaction of 4a with methyl lithium. The lithium vinyl group may then be functionalized by reaction with an alkoxycarbonyl chloride.

The 7-carboxylmethylene compounds (R$_1$ or R$_2$=COOH or COOY) may be formed by hydrolysis of the corresponding ester, preferably, the corresponding t-butyl ester.

The compounds wherein R$_3$ is a halogen may be formed by displacement of the —OAc group with ethylxanthate (EtOCS$_2$K). Raney-Nickel desulfurization (H$_2$/Ra-Ni) would yield the exocyclic alkene which may then be ozonized to the 3-hydroxy cephem. Reaction with a halogenating reagent would provide the 3-halo species. For example, PCl$_5$ may be used to convert the 3-OH group into a 3-Cl group. The 3-methyl species may be obtained by the rearrangement of the exocyclic alkene, formed by Raney-Nickel desulfurization, by reaction with Et$_3$N. The 3-hydroxymethyl species may be obtained by hydrolysis of the —OAc group with NaOH or an appropriate enzyme. The 3-halomethyl species may be formed by reaction of the 3-hydroxymethyl species with a halogenating reagent. For example, PCl$_5$ may be used to form the 3-chloromethyl species.

The compounds wherein M is alkoxy, aryloxy, or arylalkoxy may be obtained by reaction of the 3-hydroxymethyl species with tosyl chloride and displacement of the resultant tosylate with an oxide. For example, sodium methoxide may be used to obtain the 3-methoxymethyl species. The compounds wherein M is mercapto may be formed by reaction of the 3-chloromethyl compound with sodium sulfhydride (NaSH). This compound may further be derivatized with an alkylhalide to form a substituted mercapto or an acylchloride to form an acylthio group.

The species wherein M is an amino group may be formed by the Gabriel Synthesis, i.e., reaction of the 3-chloromethyl compound with potassium phthalimide and hydolysis of the product with acid to yield the 3-aminomethyl compound. The 3-ammoniomethyl compound may be formed by reaction of the 3-aminomethyl compound with methyl chloride to form the 3-trimethylammoniomethyl chloride.

The compound wherein M is an amido group (CONH$_2$) may be formed by displacement of the tosylate described above with cyanide, e.g. KCN, followed by hydrolysis of the resulting nitrile to the amide.

The aforementioned salts of 7-alkylidene cephems were evaluated as inhibitors of the Class C β-lactamase of Enterobactor cloacae P99 and TEM2 by relative IC$_{50}$ analysis. The IC$_{50}$ value represents the concentration of inhibitor required to effect a 50% loss of activity of free enzyme. The IC$_{50}$ value of each compound was determined as follows. Following a 10 minute incubation of a dilute solution of enzyme (2.56 nM) and inhibitor (<0.64 mM), a 50 mL aliquot of this incubation mixture was then further diluted into 1 mL nitrocefin solution, and the rate of hydrolysis was measured during a 1 minute period by monitoring the absorbance of nitrocefin as a function of time. In addition, the IC$_{50}$ values of tazobactam and clavulanic acid were determed as relative controls. The data is presented in Table 1 below.

TABLE 1

E. cloacae P99 and SC 12368, and E. coli. W3310 β-lactamase inhibitory activity

| Compound | n | $R_1$ | $R_2$ | $IC_{50}$ (nM) E. cloacea P99 | $IC_{50}$ (nM) E. coli WC3310 | $IC_{50}$ (nM) E. cloacea SC12368 |
|---|---|---|---|---|---|---|
| tazobactam | | | | 943 | 25 | 4000 |
| Clavulanic acid | | | | >20000 | 60 | >20000 |
| 6a | 0 | Br | Br | >20000 | >20000 | >20000 |
| 6b | 0 | Cl | Cl | >20000 | >20000 | >20000 |
| 6d | 0 | Ph | H | >20000 | >20000 | >20000 |
| 6e | 0 | 2'-Py | H | >20000 | >20000 | >20000 |
| 6g | 0 | $CO_2C(CH_3)_3$ | H | 2500 | >20000 | >20000 |
| 6h | 0 | $COCH_3$ | H | >20000 | >20000 | >20000 |
| 6i | 0 | CHO | H | 8200 | >20000 | 16500 |
| 6k | 0 | $CON(CH_3)$-$(OCH_3)$ | H | >20000 | >20000 | >20000 |
| 6l | 0 | H | Br | >20000 | >20000 | >20000 |
| 6m | 0 | t-Bu | H | >20000 | >20000 | >20000 |
| 7a | 1 | Br | Br | >20000 | >20000 | >20000 |
| 7b | 1 | Cl | Cl | >20000 | 8300 | >20000 |
| 7c | 1 | H | Ph | >20000 | >20000 | >20000 |
| 7d | 1 | Ph | H | 6250 | >20000 | 6800 |
| 7e | i | 2'-Py | H | 25 | 800 | 25 |
| 7f | 1 | $CO_2CH_3$ | H | >20000 | 8 | >20000 |
| 7g | 1 | $CO_2C(CH_3)_3$ | H | 7800 | 5 | 5900 |
| 7j | 1 | $CH_2OH$ | H | >20000 | >20000 | >20000 |
| 7l | 1 | H | Br | >20000 | >20000 | >20000 |
| 7m | 1 | t-Bu | H | >20000 | >20000 | >20000 |

Compound 7e, 7-(Z)-[(2-pyridyl)methylene] cephalosporanic acid sulfone, was determined to be more potent than tazobactam, showing a 20 fold increase in activity. In general, it was found that the sulfones were more potent than their corrosponing sulfide analogs. One striking example of this is the 1300 fold increase in activity of 7e, the pyridyl sulfone, over it's sulfide 6e.

In a second embodiment, the present invention provides pharmaceutical compositions useful for inhibiting a β-lactamase. The present pharmaceutical compositions comprise at least one of the present 7-alkylidene cephalosporins and at least one pharmaceutically acceptable carrier.

The present compositions may be employed in capsule form or as tablets, powders or liquid solutions or as suspensions or elixirs. They may be administered orally, intravenously or intramuscularly. The present compositions are preferably presented in a form suitable for absorption by the gastro-intestinal tract.

Tablets and capsules for oral administration may be in unit dose presentation form, and may contain conventional pharmaceutical carriers such as binding agents, for example, syrup, acacia, gelatin, sorbitol, tragacanth, or polyvinylpyrrolidone; fillers, for example, lactose, sugar, maize-starch, calcium phosphate, sorbitol or glycine, lubricants, for example, magnesium stearate, talc, polyethylene glycol, silica; disintegrants, for example, potato starch; or acceptable wetting agents such as sodium lauryl sulphate. The tablets may be coated according to methods well known in the art. Oral liquid preparations may be in the form of aqueous or oily suspensions, solutions, emulsions, syrups, elixirs, etc. or may be presented as a dry product, for reconstitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible fats; emulsifying agents, for example lecithin, sorbitan monooleate or acacia; non-aqueous vehicles, which may include edible oils, for example, almond oil, fractionated coconut oil, oily esters, propylene glycol, or ethyl alcohol; preservatives, for example, methyl or propyl p-hydroxybenzoates or sorbic acid. Suppositories will contain conventional suppository bases, e.g., cocoa butter or other glyceride.

Compositions for injection may be presented in unit does form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The present compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops, etc. Topical applications may be formulated in hydrophobic or hydrophilic bases as ointments, creams, lotions, paints, powders, etc.

Also, in addition to a carrier, the present compositions may include other ingredients such as stabilizers, binders, antioxidants, preservatives, lubricators, suspending agents, viscosity agents or flavoring agents and the like.

For veterinary medicine, the composition may, for example, be formulated as an intramammary preparation in either long acting or quick-release bases.

The dosage to be administered depends to a large extent upon the condition of the subject being treated and the weight of the subject, the route and frequency of administration, the parenteral route being preferred for generalized infections and the oral route for intestinal infections.

The instant compositions may be administered in several unit dosage forms as, for example, in solid or liquid orally ingestible dosage form. The compositions per unit dosage, whether liquid or solid may contain from 0.1% to 99% of active material (the present 7-alkylidene cephalosporins and optional antibiotic), the preferred range being from about 10–60%. The composition will generally contain from about 15 mg to about 1500 mg by weight of active ingredient based upon the total weight of the composition; however, in general, it is preferable to employ a dosage amount in the range of from about 250 mg to 1000 mg. In parenteral administration the unit dosage is usually the pure compound in a slightly acidified sterile water solution or in the form of a soluble powder intended for solution.

The present β-lactamase inhibitors will be particularly useful in the treatment of infections caused by Enterobacter, Citrobacter, and Serratia. These bacteria have the ability to attach to the epithelial cells of the bladder or kidney (causing urinary tract infections) and are resistant to multiple antibiotics including amoxicillin and ampicillin. The present β-lactamase inhibitors would also be useful in the treatment of infections caused by highly resistant Pneumococci. Such diseases include otitis media, sinusitis, meningitis (both in children and adults), bacteremia, and septic arthritis. Resistant pneumococcal strains have surfaced in many parts of the world. For example, in Hungary, 58% of S. pneumoniae are resistant to penicillin, and 70% of children who are colonized with S. pneumoniae carry resistant strains that are also resistant to tetracycline, erythromycin, trimethoprin/sulfamethoxazole (TMP/SMX), and 30% resistant to chloroanphenicol. *Klebsiella pneumoniae* (resistant via the production of β-lactamase) have caused hospital outbreaks of wound infection and septicemia.

Thus, in a third embodiment, the present invention provides pharmaceutical compositions with increased β-lactam antibiotic activity. This pharmaceutical composition is as defined above, but in addition to at least one of the present 7-alkylidene cephalosporins and at least one a pharmaceutically acceptable carrier, the compositions also contains at least one β-lactam antibiotic. The β-lactam antibiotic may be any of the above-noted antibiotics or any other known in the art, preferably amoxicillin or piperacillin, and its selection will depend upon what indication is necessary.

In a fourth embodiment, the present invention provides a method of inhibiting a β-lactamase, comprising administering to a patient in need thereof an effective amount of at least one of the present 7-alkylidene cephalosporins. The method of administration may be any of the above-noted methods or any other known to one of skill in the art.

In a fifth embodiment, the present invention provides a method of enhancing the biological activity of a β-lactam antibiotic by coadministering to a patient in need thereof, an effective amount of one of the present 7-vinylidene cephalosporins and an effective amount of at least one β-lactam antibiotic. The method of administration may be any of the above-noted methods or any other known to one of skill in the art. The β-lactam antibiotic may be any of the above-noted β-lactam antibiotics or any other known in the art.

Other features of the invention will become apparent in the course of the following descriptions of exemplary embodiments which are given for illustration of the invention and are not intended to be limiting thereof.

EXAMPLES

Example 1

Benzhydryl 7β-aminocephalosporanate (2)

To a suspension of 7-aminocephalosporanic acid (130.4 g, 0.48 mol) in methanol (480 mL) was added a solution of diphenyldiazomethane (93.0 g, 0.48 mol) in $CH_2Cl_2$, prepared by the oxidation of benzophenone hydrazone by mercury oxide at room temperature. The reaction was then mechanically stirred at room temperature for 44 hours. The remaining solid was removed by filtration. The resultant filtrate was concentrated in vacuo and purified by column chromatography (10% $CH_3OH$ in $CH_2Cl_2$) to afford the desired ester as pale yellow solid (86.1 g, 41% yield). $R_f$=0.44 in 1:9 $CH_3OH:CH_2Cl_2$, mp. 45–46° C.; IR ($CHCl_3$) 2980, 1780, 1730 $cm^{-1}$; $^1H$ NMR ($CDCl_3$) δ 8.41 (2H, bs), 7.22 (10H, m), 6.91 (1H, s), 5.27 (1H, d, J=2.8 Hz), 5.15 (1H, d, A of ABq, J=14 Hz), 4.94 (1H, s), 4.84 (1H, d, B of ABq, J=14 Hz), 3.73 (1H, d, A of ABq, J=17 Hz), 3.33 (1H, d, B of ABq, J=17 Hz), 1.92 (3H, s); $^{13}C$ NMR ($CDCl_3$) δ 169.8, 168.8, 160.6, 138.9, 138.7, 129.5, 129.3, 129.1, 128.7, 128.5, 127.97, 127.61, 127.52, 127.18, 126.52, 126.06, 125.4, 79.0, 63.3, 62.6, 58.5, 25.7, 20.1.

Example 2

Benzhydryl 7-oxocephalosporanate (3)

The title compound was prepared by modifying the procedure of Haqiwara et al. To a solution of benzhydryl 7β-aminocephalosporanate, (5.9 g, 13.5 mmol) in anhydrous $CH_2Cl_2$ (70 mL) at −78° C., triethylamine (5.6 mL, 40.4 mmol) was added dropwise with stirring. After 5 minutes, trifluoromethanesulfonic anhydride (6.8 mL, 40.4 mmol) was added dropwise to this solution over a 5 minute period. The reaction mixture was allowed to warm slowly to 0° C. over a 1 hour period. It was then recooled to −78° C. and triethylamine (5.6 mL, 40.4 mmol) was added over approximately 10 minutes. The reaction mixture was stirred at −78° C. for an additional 30 minutes and poured into 200 mL cold 0.5 N HCl. The resultant mixture was further stirred until the ice melted. The layers were separated and the aqueous layer was extracted with $CH_2Cl_2$ (150 mL). The combined organic layers were washed with cold 0.5 N HCl (3×100 mL), dried ($Na_2SO_4$), and concentrated (at room temperature or below) to produce the title compound (5.8 g, 98% yield) as a brown solid which was used without further purification. IR ($CHCl_3$) 3005, 1830, 1790, 1740 $cm^{-1}$; $^1H$ NMR ($CDCl_3$) δ 7.39 (10H, m), 7.05 (1H, s), 5.32 (1H, s), 5.07 (1H, d, A of ABq, J=14 Hz), 4.85 (1H, d, B of ABq, J=14 Hz), 3.64 (1H, d, A of ABq, J=18 Hz), 3.44 (1H, d, B of ABq, J=18 Hz), 2.05 (3H, s); $^{13}C$ NMR ($CDCl_3$) δ 188.4 (s), 170.3 (s), 160.1 (s), 158.7 (s), 138.8 (s), 138.6 (s), 128.4, 128.2, 128.1, 127.7, 126.9, 126.2, 80.1 (d), 65.8 (d), 62.6 (t), 27.7 (t), 20.4 (q).

Example 3

Benzhydryl 7-(dibromomethylene)cephalosporanate (4a)

To the solution of $Ph_3P$ (12.0 g, 45.8 mmol) in anhydrous $CH_2Cl_2$ (75 mL) was added $CBr_4$ (7.6 g, 22.9 mmol) in one portion at 0° C. The mixture was stirred at room temperature for 30 minutes. The reaction mixture was then cooled to −78° C. and a cold (−78° C.) solution of benzhydryl 7-oxocephalosporanate 3 (5.00 g, 11.4 mmol) in anhydrous $CH_2Cl_2$ (40 mL) was added. After stirring at −78° C. for 30 minutes, the reaction was concentrated in vacuo and purified by column chromatography ($CH_2Cl_2$) to give a pale yellow solid (4.1 g, 61% yield). $R_f$=0.55 in $CH_2Cl_2$; mp 58–60° C.; IR ($CHCl_3$) 3030, 1780, 1745 $cm^{-1}$; $^1H$ NMR ($CDCl_3$) δ 7.37 (10H, m), 6.96 (1H, s), 5.19 (1H, s), 4.97 (1H, d, A of ABq, J=13 Hz), 4.72 (1H, d, B of ABq, J=13 Hz), 3.52 (1H, d, A of ABq, J=18 Hz), 3.32 (1H, d, A of ABq, J=18 Hz), 2.00 (3H, s); $^{13}C$ NMR ($CDCl_3$) δ 170.2 (s), 160.5 (s), 155.6 (s), 142.6 (s), 139.1 (s), 138.9 (s), 128.4, 128.0, 127.9, 127.0, 126.7, 125.2 (s), 92.6 (s), 79.9 (d), 63.0 (t), 60.1 (d), 27.0 (t), 20.5 (q). Anal. Calcd for $C_{24}H_{19}NO_5SBr_2$: C, 48.57; H, 3.20; N, 2.36; Found: C, 48.52; H, 3.17; N, 2.19.

Example 4

Benzhydryl 7-(dichloromethylene)cephalosporanate (4b)

$CCl_4$ (2 mL, 20.7 mmol) was added into a solution of $PPh_3$ in anhydrous $CH_3CN$ (50 mL) and stirred at room temperature for 30 minutes. This solution was transferred into a solution of benzhydryl 7-oxocephalosporanate 3 (3.0 g, 8.9 mmol) in anhydrous $CH_3CN$ (20 mL) and Zn/Cu (1.0 g, 15 mmol) was added. This reaction mixture was further stirred at room temperature for 40 minutes. The unreacted Zn/Cu was removed by filtration and the filtrate was concentrated and purified by column chromatography ($CH_2Cl_2$) to yield a pale yellow solid (2.70 g, 78%). $R_f$=0.73 in $CH_2Cl_2$; mp 48–50° C.; IR ($CHCl_3$) 3050, 1780, 1740, 940 $cm^{-1}$; $^1H$ NMR ($CDCl_3$) δ 7.38 (10H, m), 6.99 (1H, s) 5.29 (1H, s), 5.02 (1H, d, A of ABq, J=13 Hz), 4.76 (1H, d, B of ABq, J=13 Hz), 3.57 (1H, d, A of ABq, J=18 Hz) 3.88 (1H, d, B of ABq, J=18 Hz), 2.04 (3H, s); $^{13}C$ NMR ($CDCl_3$) δ 170.0 (s), 160.2 (s), 154.5 (s), 138.8 (s), 138.7 (s), 136.2 (s), 128.1, 127.7, 127.2, 126.6, 126.2, 124.7 (s), 123.6 (s), 79.8 (d), 62.8 (t), 57.4 (d), 26.9 (t), 20.3 (q); high-resolution mass spectrum for $[C_{24}H_{19}NO_5SCl_2Na]^+$, i.e. $[M+Na]^+$, m/z calcd 526.0259, found 526.0251.

Example 5

Benzhydryl 7-[(E)-benzylidene]cephalosporanate and benzhydryl 7-[(Z)-benzylidene] cephalosporanate (4c)

To a solution of triphenylbenzyl phosphonium bromide (11.44 g, 26.4 mmol) in anhydrous THF (50 mL) was added a solution of n-BuLi (14.5 mL, 29.0 mmol) at −78° C. The mixture was stirred at room temperature for 30 minutes. The resulting red colored solution was recooled to −78° C. and was added to a cold (−78° C.) solution of 7-oxocephalosporanate 3 (10.5 g, 24.0 mmol) in anhydrous THF (25 mL) and stirred at −78° C. for 5 minutes. The cold reaction mixture was then poured into ice cold saturated NH$_4$Cl solution (25 mL) and the layers were separated. The aqueous layer was extracted with ether (2×50 mL). The combined organic layers were washed with water (25 mL), dried (Na$_2$SO$_4$), concentrated and purified by column chromatography (CH$_2$Cl$_2$: Hexane, 3:1) to give the E-isomer (0.83 g, 40%), and the Z-isomer (1.26 g, 60%) as white fluffy solid.

7-(E)-isomer. $R_f$=0.60 in CH$_2$Cl$_2$; mp 59–61° C.; IR (CHCl$_3$) 3015, 1760, 1730 cm$^{-1}$; $^1$H NMR (CDCl$_3$) δ 7.83 (2H, m), 7.26 (13H, m), 6.93 (1H, s), 6.53 (1H, s), 4.99 (1H, s), 4.78 (1H, d, A of ABq, J=13 Hz), 4.53 (1H, d, B of ABq, J=13 Hz), 3.39 (1H, d, A of ABq, J=18 Hz), 3.19 (1H, d, B of ABq, J=18 Hz), 1.85 (3H, s); $^{13}$C NMR (CDCl$_3$) δ 170.2 (s), 161.1 (s), 158.7 (s), 139.3 (s), 139.1 (s), 136.0 (s), 134.0 (d), 133.1, 130.3, 128.6, 128.3, 128.0, 127.7, 127.0, 121.7 (s), 79.6 (d), 63.1 (t), 56.1 (d), 27.9 (t), 20.5 (q). Anal. Calcd for C$_{30}$H$_{25}$NO$_5$S: C, 70.45; H, 4.89; N, 2.74. Found: C, 70.80; H, 5.03; N, 2.95.

7-(Z)-isomer. $R_f$=0.50 in CH$_2$Cl$_2$; mp 45–47° C.; IR (CHCl$_3$) 3025, 1790, 1760 cm$^{-1}$; $^1$H NMR (CDCl$_3$) δ 7.43 (15H, m), 7.21 (1H, d, J=1.18 Hz), 7.07 (1H, s), 5.50 (1H, d, J=1.23 Hz), 5.00 (1H, d, A of ABq, J=13 Hz), 4.75 (1H, d, B of ABq, J=13 Hz), 3.65 (1H, d, A of ABq, J=18 Hz), 3.41 (1H, d, B of ABq, J=18 Hz), 2.04 (3H, s); $^{13}$C NMR (CDCl$_3$) δ 170.3 (s), 161.0 (s), 160.2 (s), 139.3 (s), 139.1 (s), 135.8(s), 132.4 (d), 130.5, 129.7, 129.0, 128.3, 128.1, 127.9, 127.7, 127.0, 121.7(s), 79.7 (d), 63.1 (t), 57.7 (d), 28.0 (t), 20.5 (q); high-resolution mass spectrum for $[C_{30}H_{25}NO_5SNa]^+$, i.e. $[M+Na]^+$, m/z calcd 534.1351, found 534.1352.

Example 6

Benzhydryl 7-[(Z)-(2'-pyridyl)methylene] cephalosporanate (4e)

To a solution of 2-picolyl chloride hydrochloride (13.1 g, 80 mmol) in water (20 mL) was added into K$_2$CO$_3$ (11.0 g, 80 mmol). After the carbonate was completely dissolved, the solution was extracted with ether (3×10 mL). The combined organic layers were washed with saturated NaCl solution (1×30 mL), dried (Na$_2$SO$_4$) and concentrated to give picolyl chloride (9.2 g, 90%). Picolyl chloride (8.9 g, 70 mmol), triphenylphosphine (18.3 g, 70 mmol) and 1,4-dioxane (30 mL) were mixed and refluxed for 24 hours. The reaction mixture was washed with ether (2×30 mL) and the remaining solid was dried in vacuo to give a white solid (25.5 g, 94%). A mixture of 2-picolyltriphenylphosphonium chloride (5.8 g, 15 mmol) and sodium amide (0.58, 15 mmol) in THF (15 mL) was stirred at room temperature for 30 minutes. The resulting brown suspension was cooled to −78° C. and a solution of benzhydryl 7-oxocephalosporanate 3 (6.6 g, 15 mmol) in THF (15 mL) was added in one portion and the mixture was stirred at −78° C. for 15 minutes. The reaction was quenched by the addition of saturated ammonium chloride solution (10 mL) and the reaction mixture extracted with EtOAc (2×20 mL). The combined organic layers were washed with water (2×40 mL), dried over MgSO$_4$, concentrated and purified by column chromatography to obtain a yellow solid (2.9 g, 38%). $R_f$=0.28 in 2% EtOAc in CH$_2$Cl$_2$; mp 181–183° C.; IR (CHCl$_3$) 3060, 1810, 1750 cm$^{-1}$; $^1$H NMR (CDCl$_3$) δ 8.68 (1H, d), 7.72 (1H, t), 7.35(12H, m), 7.15 (1H, s), 7.10 (1H, s), 5.66 (1H, s), 4.96 (1H, d, A of ABq, 13 Hz), 4.73 (1H, d, B of ABq, J=13 Hz), 3.63 (1H, d, A of ABq, J=18 Hz), 3.63 (1H, D, B of ABq, J=18 Hz), 2.01 (3H, s); $^{13}$C NMR (CDCl$_3$) δ 170.3 (s), 161.0 (s), 160.2 (s), 151.6 (d), 150.1 (s), 140.6 (s), 139.3 (s), 139.1 (s), 136.6 (d), 128.3, 127.9, 127.8, 127.6, 127.2, 126.9, 125.8 (s), 123.9 (s), 123.5 (s), 79.5 (d), 63.0 (t), 58.5 (d), 28.0 (t), 20.5 (q); high-resolution mass spectrum for $[C_{29}H_{24}N_2O_5SNa]^+$, i.e. $[M+Na]^+$, m/z calcd 535.1304, found 535.1300.

Example 7

Benzhydryl 7-[(Z)-methoxycarbonylmethylene] cephalosporanate (4f)

To a solution of benzhydryl 7-oxocephalosporanate (1.0 g, 2.3 mmol) in anhydrous CH$_2$Cl$_2$ (20 mL) at −78° C. was added methyl(triphenylphosphoranylidene)acetate (0.67 g, 2.0 mmol). The mixture was then stirred at −78° C. for 30 minutes. Acetic acid (0.5 mL) was added to quench the reaction and the reaction mixture was concentrated and purified by column chromatography to give title compound as a pale yellow solid (0.67 g, 68%). $R_f$=0.42 in 2% EtOAc in CH$_2$Cl$_2$; mp 47–49° C.; IR (CHCl$_3$) 3050, 1790, 1730 cm$^{-1}$; $^1$H NMR (CDCl$_3$) δ 7.36 (10H, m), 7.00 (1H, s), 6.49 (1H, s), 5.50 (1H, s), 5.00 (1H, d, A of ABq, J=13.48 Hz), 4.76 (1H, d, B of ABq, J=13.47 Hz), 3.84 (3H, s), 3.64 (1H, d, A of ABq, J=18.75 Hz), 3.39 (1H, d, B of ABq, J=18.75 Hz), 2.03 (3H, s); $^{13}$C NMR (CDCl$_3$) δ 170.3 (s), 163.8 (s), 160.6 (s), 157.5 (s), 152.6 (s), 139.2 (s), 139.0 (s), 128.6, 128.3, 127.9, 127.6, 127.3, 126.90, 125.45 (s), 117.51 (d), 79.90 (d), 62.96 (t), 57.88 (d), 52.48 (q), 27.91 (t). 20.59 (q). Anal. Calcd for C$_{26}$H$_{23}$NO$_7$S: C, 63.29; H, 4.66; N, 2.84. Found: C, 63.47; H, 4.73; N. 2.87.

Example 8

Benzhydryl 7-[(Z)-t-butoxycarbonylmethylene] cephalosporanate (4g)

To a solution of benzhydryl 7-oxocephalosporanate in example 2 (4.0 g, 9.2 mmol) in anhydrous CH$_2$Cl$_2$ (40 mL) at −78° C. was added a solution of t-butyl(triphenylphosphoranylidene)acetate (3.45 g, 9.15 mmol in 40 mL CH$_2$Cl$_2$). The mixture was then stirred at −78° C. for 30 minutes. Acetic acid (1 mL) was added to quench the reaction and the reaction mixture was concentrated and purified by column chromatography to give title compound as a pale yellow solid (yield=55%). $R_f$=0.52 in 2% EtOAc in CH$_2$Cl$_2$. mp 48–50° C.; IR (CHCl$_3$) 3050, 1780, 1730 cm$^{-1}$; $^1$H NMR (CDCl$_3$) δ 7.36 (10H, m), 7.00 (1H, s), 6.39 (1H, s), 5.47 (1H, s), 5.00 (1H, d, A of ABq, J=13.48 Hz), 4.77 (1H, d, B of Abq, J=13.48 Hz), 3.62 (1H, d, A of ABq, J=18 Hz), 3.38 (1H, d, B of ABq, J=18 Hz), 2.02 (3H, s), 1.54 (9H, s); $^{13}$C NMR (CDCl$_3$) δ 170.2 (s), 162.4 (s), 160.5 (s), 157.8 (s), 150.1, (s), 139.0 (s), 138.8 (s), 128.3, 128.0, 127.9, 127.5, 126.9, 125.0 (s), 119.9 (d), 82.9 (s), 79.7 (d), 62.8 (t), 57.5 (d), 28.0 (q), 27.9 (t), 20.4 (q). Anal. Calcd for $C_{29}H_{29}NO_7S$: C, 65.05; H, 5.42; N, 2.62. Found: C, 64.50; H, 5.42, N, 2.62.

Example 9

Benzhydryl 7-[(Z)-acetylmiaphylene] cephalosporanate (4h)

This compound was prepared as described for compound example 8 (yield=58%). $R_f$=0.29 in 2% EtOAC in $CH_2Cl_2$; mp 49–50° C.; IR (CHCl$_3$) 3000, 1770, 1720 cm$^{-1}$; $^1$H NMR (CDCl$_3$) δ 7.36 (10H, m), 7.00 (1H, s), 6.48 (1H, s), 5.50 (1H, s), 5.00 (1H, d, A of ABq, J=13.47 Hz), 4.77 (1H, d, B of ABq, J=13.48 Hz), 3.63 (1H, d, A of ABq, J=18.75 Hz), 3.38 (1H, d, B of ABq, J=18.75 Hz). 2.39 (3H, s), 2.02 (3H, s). $^{13}$C NMR (CDCl$_3$) δ 195.8 (s), 170.3 (s), 160.6 (s), 158.5 (s), 149.5 (s), 139.3 (s), 139.1 (s), 128.5, 127.8, 127.1, 126.9, 126.3, 125.6 (s), 122.7 (d), 79.8 (d), 63.0 (t), 58.0 (d), 30.9 (q), 28.0 (t), 20.7 (q). Anal. Calcd for $C_{26}H_{23}NO_6S$: 65.41, 4.82, 2.94. Found: C, 65.89; H, 4.87; N, 3.11.

Example 10

Benzhydryl 7-[(Z)-formylmethylene] cephalosporanate (4i)

This compound was prepared as described for compound example 8 (yield=46%). $R_f$=0.37 in 2% EtOAc in $CH_2Cl_2$; mp 113–115° C.; IR (CHCl$_3$) 3050, 1780. 1730, 1700 cm$^{-1}$; $^1$H NMR (CDCl$_3$) δ 7.39 (10H, m), 6.99 (1H, s), 6.60 (1H, d, J=6.17 Hz), 5.45 (1H, s), 5.00 (1H, d, A of ABq, J=13.51 Hz), 4.75 (1H, d, B of ABq, 13.55 Hz), 3.64 (1H, d, A of ABq, J=18.59 Hz), 3.41 (1H, d, B of ABq, J=18.61 Hz), 2.00 (3H, s); $^{13}$C NMR (CDCl$_3$) δ 188.2 (d), 170.1 (s), 160.3 (s), 157.0 (s), 154.7 (s), 138.9 (s), 138.8 (s), 128.4, 128.1, 128.0, 127.6, 126.9, 126.7, 125.0 (s), 123.5 (d), 79.9 (d), 62.4 (t), 56.4 (d), 28.1 (t), 20.4 (q); high-resolution mass spectrum for $[C_{25}H_{21}NO_6SNa]^+$, i.e. $[M+Na]^+$, m/z calcd 486.0987, found 468.0981.

Example 11

Benzhydryl 7-[(Z)-hydroxymethylmethylene] cephalosporanate (4j)

To a solution of the formylmethylene cephalosporanate described in example 10 (0.75 g, 1.62 mmol) in methanol (10 mL) and acetic acid (1 mL) was added NaCNBH$_3$ (0.51 g, 8.1 mmol) in one portion, and stirred at room temperature for 30 minutes. The reaction mixture was concentrated in vacuo, and the residue was dissolved in EtOAc (25 mL) and water (10 mL). The aqueous layer was exacted with EtOAc (1×30 mL), and the combined organic layer was washed with water (1×30 mL), dried (Na$_2$SO$_4$), concentrated and purified by column chromatography to give a white solid (0.71 g, 94%). $R_f$=0.3 in 10% EtOAc in $CH_2Cl_2$; mp 58–60° C.; $^1$H NMR (CDCl$_3$) δ 7.39 (10H, s), 7.01 (1H, s), 6.51 (1H, s), 5.29 (1H, s), 4.94 (1H, d, A of ABq, J=13.16 Hz), 4.71 (1H, d, B of ABq, J=13.18 Hz), 4.60 (1H, d, A of ABq, J=20.83 Hz), 4.42 (1H, d, B of ABq, J=20.22 Hz), 3.56 (1H, d, A of ABq, J=18.37 Hz), 3.33 (1H, d, B of ABq, J=18.09 Hz), 2.01 (3H, s); $^{13}$C NMR (CDCl$_3$) δ 170.5 (s), 161.2 (s), 159.9 (s), 139.0 (s), 138.8 (s), 137.4 (s), 131.8 (d), 128.3, 128.0, 127.9, 127.6, 127.4, 126.8, 122.2 (s), 79.6 (d), 63.0 (t), 60.0 (t), 56.9 (d), 28.0 (t), 20.5 (q); high-resolution mass spectrum for $[C_{25}H_{23}NO_6SNa]^+$, i.e. $[M+Na]^+$, m/z calcd 488.1144, found 488.1138.

Example 12

Benzhydryl 7-[(Z)-N-methoxy-N-methylaminocarbonylmethylene]cephalosporanate (4k)

To a solution of benzhydryl 7-oxocepharosporanate (1.0 g, 2.3 mmol) in anhydrous $CH_2Cl_2$ (20 mL) at −78° C. was added N-methoxy-N-methyl-2-(triphenyl-phosphoranylidene)acetamide (0.73 g, 2.0 mmol). The mixture was stirred at −78° C. for 10 minutes, and then warmed to 0° C. and further stirred for 15 minutes. Acetic acid (0.5 mL) was added to quench the reaction, and the reaction mixture was concentrated and purified by column chromatography (2% EtOAc in $CH_2Cl_2$) to give title compound as a pale yellow solid (0.53 g, 51%). IR (CHCl$_3$) 3050, 1780, 1730 cm$^{-1}$; $^1$H NMR (CDCl$_3$) δ 7.35 (10H, m), 7.06 (1H, s), 7.00 (1H, s), 5.56 (1H, s), 4.96 (1H, d, A of ABq, J=13.40 Hz), 4.75 (1H, d, B of ABq, J=13.52 Hz), 3.75 (3H, s), 3.64 (1H, d, B of ABq, J=18.43 Hz), 3.37 (1H, d, B of ABq, J=18.97 Hz), 3.28 (3H, s), 2.01 (3H, s); $^{13}$C NMR (CDCl$_3$) δ 170.4 (s), 163.1 (s), 160.8 (s), 158.5 (s), 151.2 (s), 139.2 (s), 139.0 (s), 128.5, 128.4, 128.1, 128.0, 127.8, 127.0, 124.8 (s), 115.6 (d), 79.8 (d), 63.0 (t), 62.4 (q), 58.0 (d), 32.2 (q), 28.1 (t), 20.6 (q).

Example 13

Benzhydryl 7-[(E)-bromomethylene] cephalosporanate (41)

To a solution of 7-(dibromomethylene)cephalosporanate (1.19 g, 2 mmol) in methanol (20 mL) and THF (10 mL) was added NH$_4$Cl (8.56 g, 16 mmol) in one portion at 0° C. The mixture was stirred for 5 minutes. Zn/Cu (5.20 g, 8 mmol) was added in one portion and further stirred at room temperature for 30 minutes. The solvent was removed, and residue was extracted with ether (2×20 mL). The obtained ether was washed with water (1×20 mL) and brine (1×10 mL), dried (Na$_2$SO$_4$), concentrated and purified by column chromatography (CH$_2$Cl$_2$) to give a white solid (0.86 g, 83% yield). $R_f$=0.41 in $CH_2Cl_2$; mp 48–50° C.; IR (CHCl$_3$) 3025, 1780, 1730 cm$^{-1}$; $^1$H NMR (CDCl$_3$) δ 7.32 (10H, m), 6.96 (1H, s), 6.44 (1H, s), 5.05 (1H, s) 4.92 (1H, d, A of ABq, J=13.37 Hz), 4.67 (1H, d, B of ABq, J=13.36 Hz), 3.46 (1H, d, A of ABq, J=18.31 Hz), 3.26 (1H, d, B of ABq, J=18.37 Hz), 1.96 (3H, s); $^{13}$C NMR (CDCl$_3$) δ 170.15 (s), 160.60 (s), 157.04 (s), 141.77 (s), 139.05 (s), 138.86 (s), 128.32, 127.97, 127.89, 127,49, 126.92, 123.30 (s), 107.94 (d), 79.82 (d), 62.90 (t), 58,02 (d), 27.68 (t), 20.42 (q). Anal. Calcd for $C_{24}H_{20}NO_5SBr$: C, 56.03; H, 3.89; N, 2.72. Found: C, 56.29; H, 3.87; N, 2.63.

Example 14

Benzhydryl 7-[(Z)-t-butylmethylene] cephalosporanate (4m)

To a suspension of CuCN (1.65 g, 3.2 mmol) in anhydrous THF (50 mL) at −78° C. was added t-BuLi (3.8 mL, 4.2 mmol). The cooling bath was removed until all the solid had gone into the solution. This cuprate solution was cooled to −78° C. and a solution of benzhydryl 7-(E)-bromomethylene cephalosporanate (1.65 g, 3.2 mmol in anhydrous THF, 15 mL) at −78° C. was cannulated to the cuprate solution as fast as possible. The solution was stirred at −78° C. for 1 minutes before quenching with saturated NH$_4$Cl solution (20 mL). The reaction mixture was extracted with ether (50 mL). The combined organic layers were washed with cold saturated NH$_4$Cl (2×10 mL), dried aver Na$_2$SO$_4$, concentrated, and purified by column chromatography (CH$_2$Cl$_2$) to give a white solid (1.23 g, 78% yield). $R_f$=0.64 in $CH_2Cl_2$; mp 120–121° C.; IR (CHCl$_3$) 2950, 1765, 1730 cm$^{-1}$; $^1$H NMR (CDCl$_3$) δ 7.35 (10H, m), 7.00 (1H, s), 6.00 (1H, s), 4.93 (1H, s), 4.86 (1H, d, A of ABq, J=13.07 Hz), 4.63 (1H, d, B of ABq, J=13.05 Hz), 3.48 (1H, d, A of ABq, J=18.30 Hz), 3.28 (1H, d, B of ABq, J=18.32 Hz), 1.96 (3H, s), 1.24 (9H, s); $^{13}$C NMR (CDCl$_3$) δ 170.30 (s), 161.44 (s), 158.31 (s), 147.87 (d), 139,30 (s), 139.08 (s), 135.76 (s), 128.31, 128.02, 127.80, 127.03, 121.01 (s), 79,50 (d), 63.10 (t), 55.72 (d), 34.43 (s), 29.83 (q), 27.86 (t), 20.50 (q). Anal. Calcd for C$_{28}$H$_{29}$NO$_5$S: C, 68.43; H, 5.91; N, 2.85. Found: C, 67.98; H, 5.90; N, 2.72.

Example 15

Benzhydryl 7-[dibromomethylene]cephalosporanate Sulfone (5a)

To a solution of the corrsponding sulfide 4a (0.3 g, 0.5 mmol) in CH$_2$Cl$_2$ (10 mL) and pH=6.4 Buffer solution (10 mL) was added m-CPBA (85%, 0.35 g, 2.0 mmol) in one portion. The mixture was stirred at room temperature for 40 minutes, and then ether (50 mL) was added. After separating layers, the organic layers were washed with saturated NaHCO$_3$ (3×30 mL), dried (NaSO$_4$), concentrated and purified by column chromatography to yield a white solid (2.5 g, 79%). R$_f$=0.50 in 2% EtOAc in CH$_2$Cl$_2$; mp 62–64° C.; IR (CHCl$_3$) 3030, 1800, 1740, 1350, 1130 cm$^{-1}$; $^1$H NMR (CDCl$_3$) δ 7.36 (10H, m), 6.95 (1H, s), 5.20 (1H, s), 5.03 (1H, d, A of ABq, J=14.18 Hz), 4.68 (1H, d, B of ABq, J=14.16 Hz), 4.02 (1H, d, A of ABq, J=18.38 Hz), 3.77 (1H, d, B of ABq, J=18.40 Hz), 2.02 (3H, s); $^{13}$C NMR (CDCl$_3$) δ 170.1 (s), 159.6 (s), 154.8 (s), 138.8 (s), 138.7 (s), 135.2 (s), 128.6, 128.3, 127.5, 127.1, 126.4, 125.5 (s), 124.1(s), 98.2 (s), 80.8 (d), 73.0 (d), 62.0 (t), 52.1 (t), 20.5 (q). Anal. Calcd for C$_{24}$H$_{19}$NO$_7$SBr$_2$: C,46.08; H, 3.04; N, 2.24; Br, 25.60. Found: C, 46.29; H, 3.09; N, 2.13, Br, 26.18.

Example 16

Benzhydryl 7-[dichloromethylene]cephalosporanate Sulfone (5b)

This compound was prepared form the corresponding sulfide 4b as described for the compound in example 15 to give a white solid (yield=81%). R$_f$=0.38 in 2% EtOAc in CH$_2$Cl$_2$; mp 64–66° C.; IR (CHCl$_3$) 3050, 1800, 1740, 1350, 1140 cm$^{-1}$; $^1$H NMR (CDCl$_3$) δ 7.35 (10H, m), 6.95 (1H, s), 5.28 (1H, s), 5.05 (1H, d, A of ABq, 14.14 Hz), 4.65 (1H, d, B of ABq, 13.90 Hz), 4.03 (1H, d, A of ABq, J=18.08 Hz), 3.80 (1H, B of ABq, 17.74 Hz), 2.04 (3H, s); $^{13}$C NMR (CDCl$_3$) δ 170.2 (s), 159.6 (s), 153.9 (s), 138.6 (s), 138.5 (s), 134.3 (s), 130.2 (s), 128.9, 128.6, 128.3, 127.6, 127.3, 127.1, 124.3 (s), 80.7 (d), 70.7 (d), 61.9 (t), 51.7 (t), 20.5 (q). Anal. Calcd for C$_{24}$H$_{19}$NO$_7$SCl: C, 53.73; H, 3.54; N, 2.61. Found: C, 53.36; H, 3.78; N, 2.47.

Example 17

Benzhydryl 7-[(E)-benzylidene]cephalosporanate Sulfone (5c)

This compound was prepared from the sulfide 4c (0.51 g, 1.0 mmol) as described for the compound in example 15 to give a white solid (0.350 g, yield=65%). R$_f$=0.27 in CH$_2$Cl$_2$. mp 194–196° C.; IR (CHCl$_3$) 2975, 1775, 1730, 1340, 1125 cm$^{-1}$; $^1$H NMR (CDCl$_3$) δ 8.00 (2H, m), 7.41 (13H, m), 7.03 (1H, s), 6.94 (1H, s), 5.24 (1H, s), 5.04 (1H, d, A of ABq, J=13.91 Hz), 4.70 (1H, d, B of ABq, J=13.98 Hz), 4.05 (1H, d, A of ABq, J=17.96 Hz), 3.77 (1H, d, B of ABq, J=18.13 Hz), 2.05 (3H, s). $^{13}$C NMR (CDCl$_3$) δ 170.3 (s), 160.1(s), 157.7 (s), 138.9 (s), 138.8 (s), 138.5(d), 132.5, 131.5, 131.0, 128.9, 128.6, 128.3, 127.7, 127.1, 126.7, 122.8 (s), 80.4 (d), 69.5 (d), 62.1 (t), 51.2 (t), 20.5 (q); high-resolution mass spectrum for [C$_{30}$H$_{25}$NO$_7$SNa]$^+$, i.e. [M+Na]$^+$, m/z calcd 566.1249, found 566.1248.

Example 18

Benzhydryl 7-[(Z)-benzylidene]cephalosporanate Sulfone (5d)

This compound was prepared from the sulfide 4d (0.68 g, 1.3 mmol) as described for the compound in example 15 to give a white solid (yield=57%, 0.410 g). R$_f$=0.40 in CH$_2$Cl$_2$. MP 61–63° C. IR (CHCl$_3$) 3025, 2925, 1780, 1730, 1340, 1130 cm$^{-1}$; $^1$H NMR (CDCl$_3$) δ 7.42 (15H, m), 7.12 (1H, s), 6.98 (1H, s), 5.53 (1H, s), 4.95 (1H, d, A of ABq, J=13.80 Hz), 4.65 (1H, d, B of ABq, J=13.92 Hz), 4.04 (1H, d, A of ABq, J=18.33 Hz), 3.77 (1H, d, B of ABq, J=18.50 Hz), 1.96 (3H, s); $^{13}$C NMR (CDCl$_3$) δ 170.1 (s), 159.9 (s), 159.7 (s), 138.8 (s), 138.7 (s), 134.12 (s), 131.6 (d), 131.0, 129.8, 129.1, 128.4, 128.2, 128.1, 127.6, 127.0, 126.7, 126.2, 121.8 (d), 80.3 (d), 71.7 (d), 691.9 (t), 51.6 (t), 20.3 (q); high-resolution mass spectrum for [C$_{30}$H$_{25}$NO$_7$SNa]$^+$, i.e. [M+Na]$^+$, m/z calcd 566.1249, found 566.1262.

Example 19

Benzhydryl 7-[(Z)-(2'-pyridyl)methylene] cephalosporanate Sulfone (5e)

This compound was prepared from the corresponding sulfide 4e (0.45 g, 0.88 mmol) as described for the compound in example 15 to give a white solid (yield=90%). R$_f$=0.26 in 2% EtOAc in CH$_2$Cl$_2$; mp 120–1.22° C.; IR (CHCl$_3$) 2975, 2950, 1780, 1720, 1340, 1130 cm$^{-1}$; $^1$H NMR (CDCl$_3$) δ 8.67 (1H, d), 7.71 (1H, t), 7.40 (13H, m), 7.00 (1H, s), 5.91 (1H, s), 5.14 (1H, d, A of ABq, J=14.07 Hz), 4.80 (1H, d, B of ABq, J=14.06 Hz), 4.11 (1H, d, A of ABq, J=17.58 Hz), 3.78 (1H, d, B of ABq, J=17.58 Hz), 2.05 (3H, s); high-resolution mass spectrum for [C$_{29}$H$_{24}$N$_2$O$_7$SNa]$^+$, i.e. [M+Na]$^+$, m/z calcd 567.1202, found 567.1198.

Example 20

Benzhydryl 7-[(Z)-t-butoxycarbonylmethylene] cephlosporanate Sulfone (5g)

This compound was prepared from the corresponding sulfide 4g as described for the compound in example 15 to give a white solid (yield=73%). R$_f$=0.68 in 5% EtOAc in CH$_2$Cl$_2$; mp 58–60° C. IR (CHCl$_3$) 3025, 1800, 1730, 1350, 1160 cm$^{-1}$; $^1$H NMR (CDCl$_3$) δ 7.36 (10H, m), 6.98 (1H, s), 6.59 (1H, s), 5.58 (1H, s), 5.14 (1H, d, A of ABq, J=14.35 Hz), 4.80 (1H, d, B of ABq, J=14.35 Hz), 4.12 (1H, d, A of ABq, J=17.58 Hz), 3.77 (1H, d, B of ABq, J=17.87 Hz), 2.04 (3H, s). 1.52 (9H, s); $^{13}$C NMR (CDCl$_3$) δ 170.0 (s), 161.5 (s), 159.4 (s), 157.1 (s), 142.3 (s), 138.6 (s), 138.5 (s), 128.8, 128.4, 128.3, 127.2, 127.0, 125.9 (s), 123.5 (d), 83.8 (s), 80.2 (d), 71.6 (d), 61.3 (t), 52.8 (t), 27.6 (q), 20.2 (q); high-resolution mass spectrum for [C$_{29}$H$_{29}$NO$_9$SNa]$^+$, i.e. [M+Na]$^+$, m/z calcd 590.1461, found 590.1447.

Example 21

Benzhydryl 7-[(Z)-acetylmethylene]cephlosporanate Sulfone (5h)

This compound was prepared from the corresponding sulfide 4h as described for the compound in example 15 to give a white solid (yield=79%). R$_f$=0.66 in 25% EtOAc in CH$_2$Cl$_2$; mp 176–178° C.; IR (CHCl$_3$) 3050, 1800, 1730, 1350, 1140 cm$^{-1}$; $^1$H NMR (CDCl$_3$) δ 7.38 (10H, m), 6.99 (1H, s), 6.94 (1H, s), 5.64 (1H, s), 5.13 (1H, d, A of ABq, J=14.51 Hz), 4.81 (1H, d, B of ABq, J=14.41 Hz), 4.12 (1H, d, A of ABq, J=17.91 Hz), 3.80 (1H, d, B of ABq, J=17.94 Hz), 2.46 (3H, s), 2.07 (3H, s). $^{13}$C NMR (CDCl$_3$) δ 194.7 (s), 170.1 (s), 159.5 (s), 157.5 (s), 141.2 (s), 138.7 (s), 138.6 (s), 128.6, 128.3, 127.5, 127.1, 126.8 (s), 125.3 (d), 80.5 (d), 72.2 (d), 61.7 (t), 53.1 (t), 31.0 (q), 20.5 (q); high-resolution mass spectrum for [C$_{26}$H$_{23}$NO$_8$SNa]$^+$, i.e. [M+Na]$^+$, m/z calcd 532.1042, found 532.1045.

Example 22

Benzhydryl 7-[(Z)-hydroxymethylmethylene] cephalosporanate Sulfone (5j)

This compound was prepared form the corresponding sulfide 4j as described in the compound in example 15 to give a white solid (yield=68%). R$_f$=0.32 in 25% EtOAc in CH$_2$Cl$_2$; mp 58–60° C.; IR (CHCl$_3$) 3050, 1780, 1730, 1330, 1130 cm$^{-1}$; $^1$H NMR (CDCl$_3$) δ 7.36 (10H, m), 6.97 (1H, s), 6.81 (1H, s), 5.53 (1H, s), 5.05 (1H, d, A of ABq, J=14.06 Hz), 4.74 (1H, d, B of ABq, J=14.06 Hz), 4.61 (1H, d, A of ABq, J=19.04 Hz), 3.98 (1H, d, B of ABq, J=19.03 Hz), 4.06 (1H, d, A of ABq, J=17.0 Hz), 3.76 (1H, d, B of ABq, J=17.80 Hz), 2.04 (3H, s); $^{13}$C NMR (CDCl$_3$) δ 170.4 (s), 160.0 (s), 158.6 (s), 138.9 (s), 138.8 (s), 136.8 (d), 128.6, 128.1, 127.8, 127.6, 127.5, 127.2, 126.7, 124.3 (s), 80.8 (d), 71.4 (d), 61.9 (t), 60.7 (t), 51.4 (t), 20.6 (q); high-resolution mass spectrum for [C$_{25}$H$_{23}$NO$_6$SNa]$^+$, i.e. [M+Na]$^+$, m/z calcd 488.1144, found 488.1138.

Example 23

Benzhydryl 7-[(Z)-N-methoxy-N-methylaminocarbonylmethylene]cephlosporanate Sulfone (5k)

This compound was prepared from the corresponding sulfide 4k as described for the compound in example 15 to give a white solid (yield=68%). R$_f$=0.44 in 25% EtOAc in CH$_2$Cl$_2$; mp 81–82° C.; IR (CHCl$_3$) 3050, 1800, 1740, 1360, 1140 cm$^{-1}$; $^1$H NMR (CDCl$_3$) δ 7.36 (10H, m), 7.28 (1H, s), 6.98 (1H, s), 5.72 (1H, s), 5.10 (1H, d, A of ABq, J=14.06 Hz), 4.82 (1H, d, B of ABq, J=14.35 Hz), 4.11 (1H, d, A of ABq, J=16.70 Hz), 3.78 (1H, d, B of ABq, J=17.58 Hz), 3.78 (3H, s), 3.31 (3H, s), 2.06 (3H, s); $^{13}$C NMR (CDCl$_3$) δ 170.1 (s), 162.1 (s), 159.7 (s), 157.8 (s), 142.78 (s), 138.9 (s), 138.8 (s), 128.7, 128.4, 127.7, 127.4, 127.1, 126.9, 125.7 (s), 119.3 (d), 80.3 (d), 72.3 (d), 62.5 (q), 61.8 (t), 52.9 (t), 32.3 (q), 20.5 (q); high-resolution mass spectrum for [C$_{27}$H$_{26}$N$_2$O$_9$SNa]$^+$, i.e. [M+Na]$^+$, m/z calcd 577.1257, found 577.1247.

Example 24

Benzhydryl 7-[(E)-bromomethylene] cephalosporanate Sulfone (5l)

This compound was prepared from the corresponding sulfide 4l as described for the compound in example 15 to give a white solid (yield=71%). R$_f$=0.43 in 2% EtOAC in CH$_2$Cl$_2$; mp 80–82° C.; IR (CHCl$_3$) 3030, 1800, 1730, 1350, 1130 cm$^{-1}$; $^1$H NMR (CDCl$_3$) δ 7.33 (10H, m), 6.94 (1H, s), 6.91 (1H, s), 5.10 (1H, s), 5.00 (1H, d, A of ABq, J=14.19 Hz), 4.67 (1H, d, B of ABq, J=14.17 Hz), 3.97 (1H, A of ABq, J=18.06 Hz), 3.69 (1H, d, B of ABq, J=18.17 Hz), 1.99 (1H, s); $^{13}$C NMR (CDCl$_3$) δ 170.1 (s), 159.7 (s), 156.3 (s), 138.7 (s), 138.6 (s), 134.0 (s), 128.4, 128.1, 127.3, 126.9, 125.7, 124.9 (s), 112.5 (d), 80.57 (d), 70.9 (d), 61.8 (t), 51.2 (t), 20.4 (q). Anal. Calcd for C$_{24}$H$_{20}$NO$_7$SBr: C, 52.75; H, 3.66; N, 2.56. Found: C, 52.78, H, 3.75; N, 2.77.

Example 25

Benzhydryl 7-[(Z)-t-butylmethylene] cephalosporanate Sulfone (5m)

This compound was prepared from the corresponding sulfide 4m as described in the compound in example 15 to give a white solid (yield=84%). R$_f$=0.48 in 2% EtOAc in CH$_2$Cl$_2$; mp 147–149° C.; IR (CHCl$_3$) 3050, 3000, 1785, 1740, 1340, 1130 cm$^{-1}$; $^1$H NMR (CDCl$_3$) δ 7.37 (10H, m), 6.97 (1H, s), 6.26 (1H, d, J=1.0 Hz), 5.01 (1H, d, J=1.0 Hz), 4.97 (1H, d, A of ABq, J=13.86 Hz), 4.65 (1H, d, B of ABq, J=13.83 Hz), 3.96 (1H, d, A of ABq, J=18.27 Hz), 3.82 (1H, d, B of ABq, J=17.95), 2.01 (3H, s), 1.29 (9H, s); $^{13}$C NMR (d$^6$-acetone) δ 170.40 (s), 160.92 (s), 158.49 (s), 152.29 (d), 140.44 (s), 140.24 (s), 128.89, 128.63, 128.00, 127.58, 126.43, 124.24 (s), 80.42 (d), 69.70 (d), 62.41 (t), 51.15 (t), 35.40 (s), 29.67 (q), 20.33 (q); high-resolution mass spectrum for [C$_{28}$H$_{29}$NO$_7$SNa]$^+$, i.e. [M+Na]$^+$, m/z calcd 546.1562, found 546.1551.

Example 26

Sodium Salt of 7-[dibromomethylene] cephalosporanic Acid (6a)

To a solution of benzhydryl 7-dibromomethylene cephalosporanate 4a (0.3 g, 0.5 mmol) in anhydrous CH$_2$Cl$_2$ (10 mL) was added anisole (0.54 mL, 5 mmol) at −78° C. followed by the addition of AlCl$_3$ solution (1.25 mL, 1.25 mmol) in one portion. The mixture was stirred at −78° C. for 15 minutes and poured into rapidly stirred cold water (30 mL) containing NaHCO$_3$ (0.42 g, 5 mmol), followed by the addition of EtOAc (30 mL). It was further stirred for 5 minutes and filtered using celite 545. The aqueous layer was separated and concentrated in vacuo to about 2 mL and purified by reverse phase chromatography followed by lyophilization to yield a pink solid (180 mg, 80%). R$_f$=0.62 in 10% EtOH in water; UV:λ$_{max}$=252 nm (50 mM phosphate buffer, pH=7.2), ϵ=14,434 cm$^{-1}$. mol$^{-1}$. l; IR (KBr) 2950, 1730, 1600, 1390 cm$^{-1}$; $^1$H NMR (d$^6$-DMSO) δ 5.42 (1H, s), 4.91 (1H, d, A of ABq, J=12.15), 4.71 (1H, d, B of ABq, J=11.89 Hz), 3.50 (1H, d, A of ABq, J=17.39 Hz), 3.22 (1H, d, B of ABq, J=17.72 Hz), 1.99 (3H, s); high-resolution mass spectrum for [C$_{11}$H$_8$NO$_5$SBr$_2$Na$_2$]$^+$, i.e. [M+Na]$^+$, m/z calcd 469.8285, found 469.8277.

Example 27

Sodium Salt of 7-[dichloromethylene] cephalosporanic Acid (6b)

This compound was prepared from the corresponding ester 4b (0.3 g, 0.6 mmol) as described in the compound in example 26 to give a pale yellow fluffy solid (yield=62%). R$_f$=0.66 in 10% EtOH in water; UV:λ$_{max}$=242 nm (50 mM phosphate buffer, pH=7.2), ϵ=11,789 cm$^{-1}$·mol$^{-1}$·l; IR (KBr) 2950, 1740, 1600, 1390 cm$^{-1}$; $^1$H NMR (d$^6$-DMSO) ϵ5.52 (1H, s), 4.93 (1H, d, A of ABq, J=12.09 Hz), 4.73 (1H, d, B of ABq, J=12.70 Hz), 3.53 (1H, d, A of ABq, J=17.65 Hz), 3.27 (1H, d, B of ABq, J=17.62 Hz), 1.99 (3H, s); high-resolution mass spectrum for [C$_{11}$H$_9$NO$_5$SCl$_2$Na]$^+$, i.e. [M+H]$^+$, m/z calcd 359.9473, found 359.9476.

Example 28

Sodium Salt of 7-[(Z)-(2'-pyridyl)methylene] cephalosporanic Acid (6c)

This compound was prepared from the corresponding ester 4c (0.4 g, 0.78 mmol) as described for the compound in example 26 to give a yellow solid (149 mg, 52%). $R_f$=0.56 in 10% EtOH in water; UV:$\lambda_{max}$=296 nm (50 mM phosphate buffer, pH=7.2), $\epsilon$=11,257 cm$^{-1}$·mol$^{-1}$·l; IR (KBr) 2950, 1720, 1600, 1390 cm$^{-1}$; $^1$H NMR (d$^6$-DMSO) δ 8.64 (1H, d), 7.83 (1H, t), 7.63 (1H, d), 7.37 (1H, t), 7.34 (1H, s), 5.63 (1H, s), 4.92 (1H, d, A of ABq, J=11.43 Hz), 4.77 (1H, d, B of ABq, J=12.30 Hz), 3.56 (1H, d, A of ABq, J=17.57 Hz), 3.27 (1H, d, B of ABq, J=17.78 Hz), 2.00 (3H, s); high-resolution mass spectrum for [C$_{16}$H$_{14}$N$_2$O$_5$SNa]$^+$, i.e. [M+H]$^+$, m/z calcd 369.0518, found 369.0506.

Example 29

Sodium Salt of 7-[(Z)-methoxycarbonylmethylene] cephlosporanic Acid (6f)

To a solution of benzhydryl 7-(Z)-(methoxycarbonylmethylene) cephalosporanate 4f (0.25 g, 0.51 mmol) in anisole (1.1 mL, 15.3 mmol) at 0° C. was added trifluroacetic acid (4.6 mL, 59.7 mmol). The mixture was stirred for 10 minutes, concentrated in vacuo, dissolved in 40 mL EtOAc, and then poured into rapidly stirred NaHCO$_3$ solution (0.5 g in 30 mL H$_2$O). The aqueous layer was separated, concentrated in vacuo to 2 mL and further purified by reverse phase chromatography ($R_f$=0.84 in 5% EtOH in water) followed by lyopholization to yield a pale yellow fluffy solid (158 mg, 89%). UV:$\lambda_{max}$=226 nm (50 mM phosphate buffer, pH=7.2), $\epsilon$=12,254 cm$^{-1}$·mol$^{-1}$·l; IR (KBr) 2950, 1730, 1600, 1400 cm$^{-1}$; $^1$H NMR (d$^6$-DMSO) δ 6.47 (1H, s), 5.54 (1H, s), 4.93 (1H, d, A of ABq, J=11.71 Hz), 4.79 (1H, d, B of ABq, J=11.72 Hz), 3.37 (3H, s), 3.58 (1H, d, A of ABq, J=18.31 Hz), 3.27 (1H, d, B of ABq, J=17.58 Hz), 2.01 (3H, s); high-resolution mass spectrum for [C$_{13}$H$_{13}$NO$_7$SNa]$^+$, i.e. [M+H]$^+$, m/z calcd 350.0310, found 350.0310.

Example 30

Sodium Salt of 7-[(Z)-t-butoxycarbonylmethylene] cephlosporanic Acid (6g)

This compound was prepared from the corresponding ester 4g (0.3 g, 0.56 mmol) as described for example 29 to give a yellow fluffy solid (176 mg, 81%). $R_f$=0.53 in 5% EtOH in water; UV:$\lambda_{max}$=225 nm (50 mM phosphate buffer, pH=7.2), $\epsilon$=11,324 cm$^{-1}$·mol$^{-1}$·l; IR (KBr) 2950, 1720, 1600, 1400 cm$^{-1}$; $^1$H NMR (d$^6$-DMSO) δ 6.26 (1H, s), 5.47 (1H, s), 4.92 (1H, d, A of ABq, J=12.00 Hz), 4.72 (1H, d, B of ABq, J=12.13 Hz), 3.56 (1H, d, A of ABq, J=18.09 Hz), 3.22 (1H, d, B of ABq, J=17.74 Hz), 1.99 (3H, s), 1.47 (9H, s); high-resolution mass spectrum for [C$_{16}$H$_{18}$NO$_7$SNa$_2$]$^+$, i.e. [M+Na]$^+$, m/z calcd 414.0600, found 414.0604.

Example 31

Sodium Salt of 7-[(Z)-acetylmethylene] cephlosporanic Acid (6h)

This compound was prepared from the corresponding ester 4h (0.4 g, 0.84 mmol) as described for example 29 to give a yellow fluffy solid (217 mg, 78%). $R_f$=0.8 in 5% EtOH in water; UV:$\lambda_{max}$=235 nm (50 mM phosphate buffer, pH=7.2), $\epsilon$=9,031 cm$^{-1}$·mol$^{-1}$·l; IR (KBr) 2950, 1750, 1600, 1390 cm$^{-1}$; $^1$H NMR (d$^6$-DMSO) δ 6.68 (1H, s), 5.56 (1H, s), 4.93 (1H, d, A of ABq, J=12.02 Hz), 4.75 (1H, d, B of ABq, J=11.20 Hz), 3.56 (1H, d, A of ABq, J=17.00 Hz), 3.25 (1H, d, B of ABq, J=17.80 Hz), 2.34 (3H, s), 2.00 (3H, s); high-resolution mass spectrum for [C$_{13}$H$_{13}$NO$_6$SNa]$^+$, i.e. [M+H]$^+$, m/z calcd 334.0361, found 334.0360.

Example 32

Sodium Salt of 7-[(Z)-hydroxymethylmethylene] cephlosporanic Acid (6j)

This compound was prepared from the corresponding ester 4j (0.15 g, 0.32 mmol) as described for example 29 to give a white fluffy solid (110 mg, 81%). $R_f$=0.86 in water; UV:$\lambda_{max}$=222 nm (50 mM phosphate buffer, pH=7.2), $\epsilon$=8,768 cm$^{-1}$·mol$^{-1}$·l; IR (KBr) 2950, 1750, 1600, 1390 cm$^{-1}$; $^1$H NMR (d$^6$-DMSO) δ 6.32 (1H, s), 5.27 (1H, s), 4.90 (1H, d, A of ABq, J=12.29 Hz), 4.68 (1H, d, B of ABq, J=12.61 Hz), 4.15 (2H, s), 3.45 (1H, d, A of ABq, J=17.46 Hz), 3.22 (1H, d, B of ABq, J=16.80 Hz), 1.97 (3H, s); high-resolution mass spectrum for [C$_{12}$H$_{13}$NO$_6$SNa]$^+$, i.e. [M+H]$^+$, m/z calcd 322.0361, found 322.0348.

Example 33

Sodium of Salt of 7-[(Z)-N-methoxy-N-methylaminocarbonylmethylene]cephlosporanic Acid (6k)

This compound was prepared from the corresponding ester 4k as described for example 29 to give yellow a fluffy solid (yield=55%). $R_f$=0.81 in 5% EtOH in water; UV:$\lambda_{max}$=231 nm (50 mM phosphate buffer, pH=7.2), $\epsilon$=11,300 cm$^{-1}$·mol$^{-1}$·l; IR (KBr) 2950, 1720, 1600, 1390 cm$^{-1}$; $^1$H NMR (d$^6$-DMSO) δ 6.84 (1H, s), 5.44 (1H, s), 4,89 (1H, d, A of ABq, J=11.88 Hz), 4.72 (1H, d, B of ABq, J=11.90 Hz), 3.72 (3H, s), 3.51 (1H, d, A of ABq, J=17,96 Hz), 3.17 (3H, s), 3.15 (1H, d, B of ABq, J=17.54 Hz), 1.98 (3H, s)

Example 34

Sodium Salt of 7-[(E)-bromomethylene] cephalosporanic Acid (6l)

This compound was prepared from the corresponding ester 4l (0.4 g, 0.78 mmol) as described for the compound in example 26 to yield a white fluffy solid (192 mg, 67%). $R_f$=0.77 in 10% EtOH in water; UV:$\lambda_{max}$=243 nm (50 mM phosphate buffer, pH=7.2), $\epsilon$=10,478 cm$^{-1}$·mol$^{-1}$·l; IR (KBr) 2950, 1730, 1600, 1390 cm$^{-1}$; $^1$H NMR (d$^6$-DMSO) δ 7.21 (1H, s), 5.28 (1H, s), 4.93 (1H, d, A of ABq, J=11.83 Hz), 4.70 (1H, d, B of ABq, 11.76 Hz), 3.48 (1H, d, A of ABq, J=17.60 Hz), 3.21 (1H, d, B of ABq, J=17.31 Hz), 1.98 (3H, s); high-resolution mass spectrum for [C$_{11}$H$_9$NO$_5$SBrNa$_2$]$^+$, i.e. [M+Na]$^+$, m/z calcd 391.9178, found 391.9180.

Example 35

Sodium Salt of 7-[(Z)-t-butylmethylene] cephalosporanic Acid (6m)

This compound was prepared from the corresponding ester 4m (0.4 g, 0.81 mmol) as described for the compound in example 26 to obtain a white fluffy solid (105 mg, 37%). $R_f$=0.55 in 10% EtOH in water; UV:$\lambda_{max}$=228 nm (50 mM phosphate buffer, pH=7.2), $\epsilon$=12,760 cm$^{-1}$·mol$^{-1}$·l; IR (KBr) 2950, 1730, 1600, 1390 cm$^{-1}$; $^1$H NMR (d$^6$-DMSO) δ 5.98 (1H, s), 5.00 (1H, s), 4.90 (1H, d, A of ABq, J=11.56 Hz), 4.68 (1H, d, B of ABq, J=11.78 Hz), 3.43 (1H, d, A of ABq, J=17.78 Hz), 3.17 (1H, d, B of ABq, J=17.45 Hz), 1.98 (3H, s), 1.17 (9H, s); high-resolution mass spectrum for [C$_{15}$H$_{19}$NO$_5$SNa]$^+$. i.e. [M+H]$^+$, m/z calcd 348.0877, found 348.0870.

Example 36

Sodium Salt of 7-[dibromomethylene] cephalosporanic Acid Sulfone (7a)

This compound was prepared from the corresponding ester 5a (0.3 g, 0.5 mmol) as described in the compound in example 26 to give a white fluffy solid (110 mg, 48%). $R_f$=0.83 in 10% EtOH in water; UV: $\lambda_{max}$=260 nm (50 mM phosphate buffer, pH=7.2), $\epsilon$=12,535 cm$^{-1}$·mol$^{-1}$·l; IR (KBr) 2950, 1740, 1600, 1390, 1330, 1130 cm$^{-1}$; $^1$H NMR (d$^6$-DMSO) δ 5.89 (1H, s), 4.94 (1H, d, A of ABq, J=12.27 Hz), 4.66 (1H, d, B of ABq, J=12.43 Hz), 4.12 (1H, d, A of ABq, J=18.29 Hz), 3.84 (1H, d, B of ABq, J=17.28 Hz), 1.99 (3H, s); high-resolution mass spectrum for [$C_{11}H_9NO_7SBr_2Na$]$^+$, i.e. [M+H]$^+$, m/z calcd 479.8361, found 479.8349.

Example 37

Sodium Salt of 7-[dichloromethylene] cephalosporanic Acid Sulfone (7b)

This compound was prepared from the corresponding ester 5b (0.4 g, 0.76 mmol) as described in the compound in example 15 to give a white fluffy solid (yield=50%). $R_f$=0.84 in 10% EtOH in water; UV: $\lambda_{max}$=245 nm (50 mM phosphate buffer, pH=7.2), $\epsilon$=16,679 cm$^{-1}$·mol$^{-1}$·l; IR (KBr) 2950, 1730, 1600, 1390, 1330, 1130 cm$^{-1}$; $^1$H NMR (d$^6$-DMSO) δ 5.99 (1H, s), 4.93 (1H, d, A of ABq, J=12.60 Hz), 4.64 (1H, d, B of ABq, J=12.30 Hz), 4.15 (1H, d, A of ABq, J=17.57 Hz), 3.90 (1H, d, B of ABq, J=18.16 Hz), 1.97 (3H, s); high-resolution mass spectrum for [$C_{11}H_8NO_7SCl_2Na_2$]$^+$, i.e. [M+Na]$^+$, m/z calcd 413.9191, found 413.9197.

Example 38

Sodium Salt of 7-[(E)-benzylidene]cephalosporanic Acid Sulfone (7c)

This compound was prepared from the corresponding ester 5c (300 mg, 0.55 mmol) as described for the compound in example 26 to give title compound as a white fluffy solid (30 mg, 13% yield). $R_f$=0.70 in 5% EtOH in water; UV: $\lambda_{max}$=308 (50 mM phosphate buffer, pH=7.2), $\epsilon$=15515 cm$^{-1}$·mol$^{-1}$·l; IR (KBr) 2950, 1710, 1600, 1390, 1330, 1130 cm$^{-1}$; $^1$H NMR (d$^6$-DMSO) δ 8.05(2H, m), 7.47 (3H, m), 6.93 (1H, s), 5.72 (1H, s), 4.95 (1H, d, A of ABq, J=12.30 Hz), 4.67 (1H, d, B of ABq, J=12.19 Hz), 4.12 (1H, d, A of ABq, J=17.60 Hz), 3.79 (1H, d, B of ABq, J=17.63 Hz), 2.00 (3H, s); high-resolution mass spectrum for [$C_{17}H_{15}NO_7SNa$]$^+$, i.e. [M+H]$^+$, m/z calcd 400.0463, found 400.0451.

Example 39

Sodium Salt of 7-[(Z)-benzylidene]cephalosporanic Acid Sulfone (7d)

This compound was prepared from the corresponding ester 5d (250 mg, 0.46 mmol) as described in the compound in example 26 to give title compound as a white fluffy solid (77 mg, 42% yield). $R_f$=0.80 in 5% EtOH in water; UV: $\lambda_{max}$=302 (50 mM phosphate buffer, pH=7.2), $\epsilon$=20543 cm$^{-1}$·mol$^{-1}$·l; IR (KBr) 2950, 1740, 1600, 1390, 1330, 1130 cm$^{-1}$; $^1$H NMR (d$^6$-DMSO) δ 7.79 (2H, m), 7.44 (4H, m), 6.34 (1H, s), 4.95 (1H, d, A of ABq, J=12.05 Hz), 4.70 (1H, d, B of ABq, J=11.75 Hz), 4.12 (1H, d, A of ABq, J=17.73 Hz), 3.88 (1H, d, B of ABq, J=17.54 Hz), 2.02 (3H, s); high-resolution mass spectrum for [$C_{17}H_{15}NO_7SNa$]$^+$, i.e. [M+H]$^+$, m/z calcd 400.0463, found 400.0464.

Example 40

Sodium Salt of 7-[(Z)-(2'-pyridyl)methylene] cephalosporanic Acid Sulfone (7e)

This compound was prepared from the corresponding ester 5e as described in as described for example 29 as a pale yellow fluffy solid (yield=67%). $R_f$=0.78 in 10% EtOH in water; UV: $\lambda_{max}$=301 nm (50 mM phosphate buffer, pH=7.2), $\epsilon$=8,624 cm$^{-1}$·mol$^{-1}$·l; IR (KBr) 2950, 1720, 1600, 1390, 1330, 1130 cm$^{-1}$; $^1$H NMR (d$^6$-DMSO) δ 8.59 (1H, d), 7.88 (1H, t), 7.72 (1H, d), 7.42 (2H, m), 6.22 (1H, s), 4.92 (1H, d, A of ABq, J=11.43 Hz), 4.72 (1H, B of ABq, J=10.87 Hz), 4.19 (1H, D, A of ABq, J=17.58 Hz), 3.77 (1H, d, B of ABq, J=18.45 Hz), 2.00 (3H, s); high-resolution mass spectrum for [$C_{16}H_{13}N_2O_7SNa_2$]$^+$, i.e. [M+Na]$^+$, m/z calcd 423.0239, found 423.0227.

Example 41

Sodium Salt of 7-[(Z)-t-butoxymethylene] cephalosporanic Acid Sulfone (7g)

This compound was prepared from the corresponding ester 5g (0.3 g, 0.53 mmol) as described in as described for example 29 to give a white fluffy solid (163 mg, 73%). $R_f$=0.74 in 5% EtOH in water; UV:$\lambda_{max}$=226 nm (50 mM phosphate buffer, pH=7.2), $\epsilon$=18,171 cm$^{-1}$·mol$^{-1}$·l; IR (KBr) 2950, 1720, 1600, 1390, 1330, 1130 cm$^{-1}$; $^1$H NMR (d$^6$-DMSO) δ 6.52 (1H, s), 5.97 (1H, s), 4.97 (1H, d, A of ABq, J=12.36 Hz), 4.72 (1H, d, B of ABq, J=12.63 Hz), 4.16 (1H, d, A of ABq, J=12.63 Hz), 3.79 (1H, d, B of ABq, J=18.21 Hz), 1.99 (3H, s), 1.45 (9H, s). high-resolution mass spectrum for [$C_{16}H_{19}NO_9SNa$]$^+$, i.e. [M+H]$^+$, m/z calcd 424.0678, found 424.0684.

Example 42

Sodium Salt of 7-[(Z)-hydroxymethylmethylene] cephalosporanic Acid Sulfone (7j)

This compound was prepared from the corresponding ester 5j (0.2 g, 0.4 mmol) as described in as described for example 29 to give a white fluffy solid (130 mg, 91.5%). $R_f$=0.90 in water; $\lambda_{max}$=223 nm (50 mM phosphate buffer, pH=7.2), $\epsilon$=9,428 cm$^{-1}$·mol$^{-1}$·l; IR (KBr) 2950, 1750, 1600, 1390, 1330, 1130 cm$^{-1}$; $^1$H NMR (d$^6$-DMSO) δ 6.54 (1H, s), 5.74 (1H, s), 4.89 (1H, d, A of ABq, J=12.05 Hz), 4.66 (1H, d, B of ABq, J=11.93 Hz), 4.14 (2H, s), 4.08 (1H, d, A of ABq, J=19.29 Hz), 3.73 (1H, d, B of ABq, J=18.25 Hz), 1.99 (3H, s); high-resolution mass spectrum for [$C_{12}H_{13}NO_8SNa$]$^+$, i.e. m/z calcd 354.0260, found 354.0274.

Example 43

Sodium Salt of 7-(E)-[bromomethylene] cephalosporanic Acid Sulfone (7l)

This compound was prepared from the corresponding ester 5l (0.3 g, 0.55 mmol) as described in the compound in example 26 to yield a white fluffy solid (128 mg, 58%). $R_f$=0.88 in 10% EtOH in water; UV: $\lambda_{max}$=246 nm (50 mM phosphate buffer, pH=7.2), $\epsilon$=10,856 cm$^{-1}$·mol$^{-1}$·l; IR (KBr) 2950, 1730, 1600, 1390, 1330, 1130 cm$^{-1}$; $^1$H NMR (d$^6$-DMSO) δ 7.44 (1H, s), 5.79 (1H, s), 4.96 (1H, d, A of ABq, J=12.30 Hz), 4.68 (1H, d, A of ABq, J=12.28 Hz), 4.03 (1H, d, A of ABq, J=18.53 Hz), 3.82 (1H, d, B of ABq, J=17.69 Hz), 2.00 (3H, s); high-resolution mass spectrum for [$C_{11}H_{10}NO_7SBrNa$]$^+$, i.e. [M+H]$^+$, m/z calcd 401.9256, found 401.9245.

Example 44

Sodium Salt of 7-[(Z)-t-butylmethylene] cephalosporanic Acid Sulfone (7m)

This compound was prepared from the corresponding ester 5m (0.34 g, 0.65 mmol) as described in the compound in example 26 to yield a white fluffy solid (2.0 g, 82%). $R_f$=0.79 in 10% EtOH in water; UV: $\lambda_{max}$=228 nm (50 mM phosphate buffer, pH=7.2), $\epsilon$=14,215 cm$^{-1}\cdot$mol$^{-1}\cdot$l; IR (KBr) 2950, 1730, 1600, 1390, 1330, 1130 cm$^{-1}$; $^1$H NMR (d$^6$-DMSO) δ 6.08 (1H, s), 5.50 (1H, s), 4.91 (1H, d, A of ABq, J=12.24 Hz), 4.65 (1H, d, B of ABq, J=12.26 Hz), 4.06 (1H, d, A of ABq, J=17.41 Hz), 3.72 (1H, d, B of ABq, J=17.76 Hz), 1.99 (3H, s); high-resolution mass spectrum for [C$_{15}$H$_{18}$NO$_7$SNa]$^+$, i.e. [M+H]$^+$, m/z calcd 380.0775, found 380.0770.

What is claimed as new and desired to be secured by Letters Patent of the United States is:

1. A compound of formula (1)

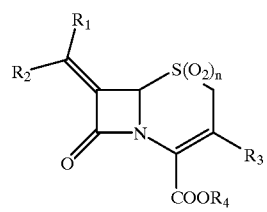

(1)

wherein n is 0;

$R_1$ and $R_2$ are the same or different and are selected from the group consisting of
   a) hydrogen;
   b) linear or branched $C_1$–$C_{10}$-alkyl;
   c) halogen;
   d) $C_{1-10}$-alkoxy;
   e) $C_{2-10}$-alkanoyloxy;
   f) $C_{2-10}$-alkene;
   g) $C_{2-10}$-alkene substituted with one or more groups selected from the group consisting of chlorine, fluorine, bromine or phenyl;
   h) $C_{1-10}$-alkoxycarbonyl;
   I) $C_{1-10}$-alkoxycarbamido;
   j) N—$C_{1-10}$-alkoxy-N—$C_{1-10}$-alkylaminocarbonyl;
   k) halo-$C_{1-10}$-alkyl;
   l) $C_{6-10}$-aryl;
   m) $C_{6-10}$-aryl; substituted with one or more groups selected from the group consisting of ethyl, n-propyl, isopropyl, amino, methylamino and dimethylamino;
   n) a $C_2$–$C_{10}$ heterocycle having from 1–3 heteroatoms selected from the group consisting of O, N, and S;
   o) —COOH or —COOY, wherein Y is pharmaceutically acceptable cation; and,
   p) COMe;

$R_3$ is —CH$_2$M where M is selected from the group consisting of
   a) $C_{2-10}$-acyloxy; and
   b) $C_{2-10}$-acyloxy substituted with one or more groups selected from the group consisting of —COOH, aminophenyl, phenyl, $C_{1-6}$-alkyl, chlorine, bromine or fluorine;

$R_4$ is selected from the group consisting of
   a) hydrogen; and,
   b) pharmaceutically acceptable cations.

2. A compound of claim 1 which is 7-[dibromomethylene] cephalosporanic acid; or a pharmaceutically acceptable salt thereof.

3. A compound of claim 1 which is 7-[dichloromethylene] cephalosporanic acid; or a pharmaceutically acceptable salt thereof.

4. The compound of claim 1, wherein $R_2$ is hydrogen and $R_1$ is selected from the group consisting of t-butyl, phenyl, pyridyl, COMe and N-methyl-N-methoxyaminocarbonyl.

5. The compound of claim 1, wherein $R_2$ is hydrogen, and $R_1$ is CO$_2$-t-Bu.

6. The compound of claim 1, wherein $R_1$ and $R_2$ are the same and are selected from the group consisting of bromine and chlorine.

7. The compound of claim 1, wherein $R_1$ is hydrogen, and $R_2$ is bromine.

8. A pharmaceutical composition, comprising a compound of claim 1 and a pharmaceutically acceptable carrier.

9. A compound of claim 1 which is: 7-[dibromomethylene] cephalosporanic acid; 7-[dichloromethylenie]cephalosporanic acid; 7-[(Z)-(2'-pyridyl)methylene] cephalosporanic acid; 7-[(Z)-methoxycarbonylmethylene]cephalosporanic acid; 7-[(Z)-t-butoxycarbonylmethylene]cephalosporanic acid; 7-[(Z)-acetylmethylene] cephalosporanic acid; 7-[(Z)-N-methoxy-N-methylaminocarbonylmethylene]cephalosporanic acid; 7-[(E)-bromomethylene]cephalosporanic acid; or 7-[(Z)-t-butylmethylene] cephalosporanic acid.

10. A compound of formula (1)

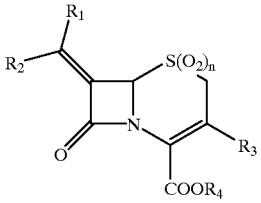

1 wherein n is 1;

$R_1$ and $R_2$ are the same or different and are selected from the group consisting of
   a) hydrogen;
   b) linear or branched $C_1$–$C_{10}$-alkyl;
   c) halogen;
   d) hydroxy-$C_{1-10}$-alkyl;
   e) $C_{1-10}$-alkoxy;
   f) $C_{2-10}$-alkanoyloxy;
   g) $C_{2-10}$-alkene;
   h) $C_{2-10}$-alkene substituted with one or more groups selected from the group consisting of chlorine, fluorine, bromine or phenyl;
   i) $C_{1-10}$-alkoxycarbonyl;
   j) $C_{1-10}$-alkoxycarbamido;
   k) N—$C_{1-10}$-alkoxy-N—$C_{1-10}$-alkylaminocarbonyl;
   l) halo-$C_{1-10}$-alkyl;
   m) $C_{6-10}$-aryl;
   n) $C_{6-10}$-aryl substituted with one or more groups selected from the group consisting of ethyl, n-propyl, isopropyl, amino, methylamino and dimethylamino;
   o) a $C_2$–$C_{10}$ heterocycle having from 1–3 heteroatoms selected from the group consisting of O, N, and S; and,
   p) —COOH or —COOY, wherein Y is pharmaceutically acceptable cation;

$R_3$ is —CH$_2$M where M is
   a) $C_{2-10}$-acyloxy; or
   b) $C_{2-10}$-acyloxy substituted with one or more groups selected from the group consisting of —COOH, aminophenyl, phenyl, $C_{1-6}$-alkyl, chlorine, bromine or fluorine; and $R_4$ is selected from the group consisting of
   a) hydrogen; and,
   b) pharmaceutically acceptable cations.

11. The compound of claim 10 wherein $R_1$ is phenyl, pyridyl or CO$_2$-t-butyl; and $R_2$ is hydrogen.

12. The compound of claim 10 wherein $R_1$ is 2-pyridyl; $R_2$ is hydrogen; M is acetoxy; and $R_4$ is sodium.

13. A pharmaceutical composition, comprising a compound of claim 10 and a pharmaceutically acceptable carrier.

* * * * *